(12) United States Patent
Cuberes Altisen et al.

(10) Patent No.: US 7,504,519 B2
(45) Date of Patent: Mar. 17, 2009

(54) DERIVATIVES OF PYRAZOLINE, PROCEDURE FOR OBTAINING THEM AND USE THEREOF AS THERAPEUTIC AGENTS

(75) Inventors: Rosa Cuberes Altisen, Sant Cugat Del Valles (ES); Jorg Holenz, Vilanova I La Geltru (ES); Mario Colombo Piñol, Barcelona (ES); Mercedes Port De Pol, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 21 days.

(21) Appl. No.: 11/571,989

(22) PCT Filed: Sep. 22, 2004

(86) PCT No.: PCT/IB2004/051822

§ 371 (c)(1),
(2), (4) Date: Jan. 12, 2007

(87) PCT Pub. No.: WO2006/011005

PCT Pub. Date: Feb. 2, 2006

(65) Prior Publication Data

US 2008/0021084 A1    Jan. 24, 2008

(30) Foreign Application Priority Data

Jul. 16, 2004    (ES) .................. 200401814

(51) Int. Cl.
- *C07D 231/06* (2006.01)
- *C07D 231/00* (2006.01)
- *A61K 31/41* (2006.01)
- *A61K 31/415* (2006.01)

(52) U.S. Cl. .............. 548/379.1; 548/356.1; 514/359; 514/403; 514/406

(58) Field of Classification Search ............... 548/356.1, 548/379.1; 514/359, 403, 406
See application file for complete search history.

(56) References Cited

FOREIGN PATENT DOCUMENTS

| WO | WO 97/38986 | 10/1997 |
|---|---|---|
| WO | WO 99/62884 | 12/1999 |
| WO | WO 00/76503 | 12/2000 |

OTHER PUBLICATIONS

Morissette, Sherry L. "High-throughput crystallization: polymorphs, salts, co-crystals and solvates of pharmaceutical solids." Advanced Drug Delivery Reviews 56(2004): 275-300.*
Vippagunta, Sudha R. "Crystalline Solids." Advanced Drug Delivery Reviews 48(2001): 3-26.*
Pal M. et al.: "Synthesis and Cyclooxygenase-2 Inhibiting Property of 1, 5-Diaryl . . . ". Journal of Medicinal Chemistry, vol. 46, No. 19, 2003, pp. 3975-3984, XP002322058.

* cited by examiner

*Primary Examiner*—Kamal A Saeed
*Assistant Examiner*—Samantha L Shterengarts
(74) *Attorney, Agent, or Firm*—WolfBlock LLP

(57) ABSTRACT

The invention relates to derivatives of general formula (I), and to their pharmaceutically acceptable salts, their stereoisomeric forms, preferably their pure enantiomeric or diastereomeric forms and their racemic forms, or a mixture thereof in any mixture ratio, and their N-oxides and the corresponding solvates or hydrates, to the processes for obtaining said derivatives and to the pharmaceutical compositions which contain them.

Said derivatives are useful as anti-inflammatory and analgesic agents.

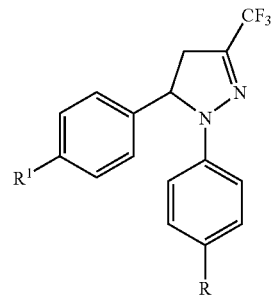

in which R and $R^1$ are different from each other and are selected from H and

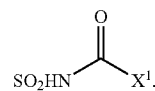

45 Claims, No Drawings

DERIVATIVES OF PYRAZOLINE, PROCEDURE FOR OBTAINING THEM AND USE THEREOF AS THERAPEUTIC AGENTS

FIELD OF THE INVENTION

This invention relates to derivatives of pyrazoline compounds, procedures for preparing them, pharmaceutical compositions which include these compounds as well as their use for the manufacture of a medicament for the treatment of pain and inflammation in human beings and animals.

BACKGROUND

Known in the art is the role that prostaglandins, metabolites of arachidonic acid, play in many physiological and pathophysiological processes such as inflammation and pain. These prostaglandins are produced from the phospholipids of the cellular membrane through a cascade of enzymes which involves the conversion of the arachidonic acid into a common precursor of the prostaglandins by means of the enzyme cyclooxygenase. Two different subtypes of cyclooxygenase are known, cyclooxygenase 1 (COX-1) and cyclooxygenase 2 (COX-2). COX-1 is the constitutive isoform mainly responsible for synthesising the gastrointestinal tract cytoprotective prostaglandins and synthesising thromboxanes, whereas COX-2 is the inducible isoform which is stimulated in response to endotoxins, cytokines, hormones, etc, that is, it is induced as a response to inflammatory processes.

For the treatment of said inflammatory processes, numerous compounds with anti-inflammatory and analgesic activity are known.

Patent application WO 99/62884 relates to a compound of general formula (I):

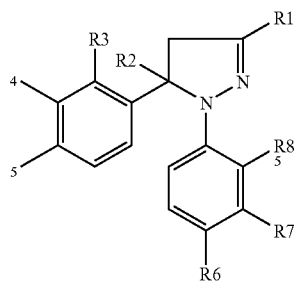

(I)

which is useful as an anti-inflammatory and analgesic.

Patent application WO 00/76503 describes a compound of general formula (V)

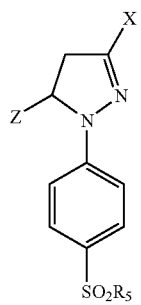

(V)

which is useful as an anti-inflammatory and analgesic.

Despite the existence of numerous compounds with anti-inflammatory and analgesic activity, there exists a need for new compounds with improved anti-inflammatory and analgesic activity.

DESCRIPTION OF THE INVENTION

This invention has the aim of providing new compounds derived from pyrazoline with improved pharmacological properties.

Under a first aspect, this invention relates to a pyrazoline derivative of general formula (I)

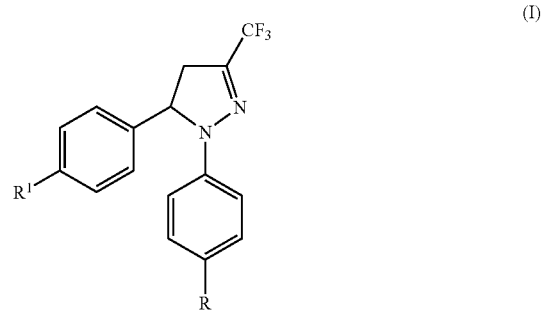

(I)

in which R and $R^1$ are different from each other and are selected from H and

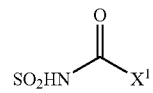

provided that when $R^1$ is H and R is

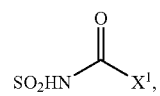

$X^1$ is an alkyl with at least one group selected from halogen, hydroxy, amine, carboxy, carboxyalkyl, acylamine or $CONH_2$; a cycloalkyl, optionally at least monosubstituted; a heterocycle; a —$OX^2$ group; a

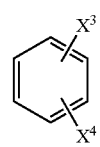

group or a heteroaryl group, optionally at least monosubstituted;

$X^2$ is an alkyl group optionally substituted by one or more substituents selected independently from the group which includes: halogen, a hydroxy group, an alcoxyl radical; a cycloalkyl group, optionally at least monosubstituted; a heterocycle group; an aryl or heteroaryl group, optionally at least monosubstituted;

$X^3$ and $X^4$ can be the same as or different from each other and are selected from H; halogen; amine; nitro; cyano; alkyl optionally substituted by one or more substituents selected from the group comprised by halogen, hydroxy group or alcoxyl radical; alcoxyl; —$CO_2X^5$; —$COX^6$; —$SO_2X^7$; an aryl or heteroaryl group, optionally at least monosubstituted;

$X^5$ is hydrogen or an alkyl radical, optionally substituted by one or more substituents selected independently from: halogen, a hydroxy group or an alcoxyl radical;

$X^6$ means an alkyl radical optionally substituted by one or more substituents selected independently from the group comprised by halogen, hydroxy group or alcoxyl radical; cycloalkyl group optionally at least monosubstituted; heterocycle group; aryl or heteroaryl group optionally at least monosubstituted;

and $X^7$ means an alkyl radical; cycloalkyl; aryl group; or heteroaryl group optionally at least monosubstituted;

and provided that when R is H and $R^1$ is

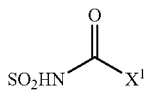

$X^1$ is an alkyl of at least two carbon atoms, optionally substituted by at least one substituent selected from halogen, hydroxy, amine, carboxy, carboxyalkyl, acylamine or $CONH_2$; cycloalkyl, optionally at least monosubstituted; heterocycle group; —$OX^2$ group;

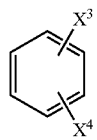

group or a heteroaryl group, optionally at least monosubstituted;

where $X^2$, $X^3$, $X^4$, $X^5$, $X^6$ and $X^7$ are as defined above; and their pharmaceutically acceptable salts, their stereoisomeric forms, preferably their pure enantiomeric or diastereomeric forms and their racemate forms, or a mixture thereof in any mixture ratio, and their N-oxides and the corresponding solvates or hydrates.

In this invention, "alkyl group" is understood as meaning a hydrocarbon chain, linear or branched, saturated or unsaturated, which contains up to 6 carbon atoms.

In this invention, "cycloalkyl group" is understood as meaning a saturated or unsaturated cyclic hydrocarbon which contains from 3 to 6 carbon atoms.

In this invention, "heterocycle group" is understood as meaning a cycloalkyl group which contains at least one heteroatom selected from the group comprised by N, O, and S, as member of the ring and which can, moreover, optionally be condensed with a mono- or polycyclic ring system, optionally at least monosubstituted.

In this invention, "heteroaryl group" is understood as meaning an aryl group of 5 or 6 atoms, in which at least one of said atoms is an atom other than carbon, with the possibility of being selected from the group comprised by N, O, and S, which can be condensed with a mono- or polycyclic ring system optionally at least monosubstituted, and optionally can be bonded via a linear or branched alkylene $C_{1-4}$ group.

"Aryl or heteroaryl optionally at least monosubstituted" is understood as meaning an aryl or heteroaryl group which can include at least one substituent selected from halogen, amine, nitro, cyano and alkyl optionally substituted with one or more substituents selected independently from the group comprised by an atom of halogen, a hydroxy group or an alcoxyl radical, or said aryl or heteroaryl group can be condensed with a mono- or polycyclic ring system optionally at least monosubstituted, and optionally can be bonded via a linear or branched alkylene $C_{1-4}$ group.

In this invention, "alcoxyl" is understood as meaning an —OZ radical, Z being a linear or branched alkyl group saturated or unsaturated, optionally substituted by one or more substituents selected from the group which comprises halogen and hydroxy radical.

In one embodiment of the first aspect of the invention, the pyrazoline derivative of formula (I) is a derivative in which when $R^1$ is H and R is

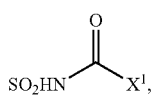

$X^1$ is an alkyl substituted by at least one group selected from halogen, hydroxy, amine, carboxy, carboxyalkyl and acylamine; cycloalkyl; —$OX^2$ group or $X^2$ is an alkyl group;

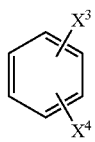

$X^3$ and $X^4$ can be the same as or different from each other and are selected from H; an aryl group at least optionally monosubstituted; haloalkyl; alcoxyl; halogen; nitro; cyano; —$CO_2X^5$; —$COX^6$ and —$SO_2X^7$;

$X^5$ is hydrogen or alkyl;

$X^6$ is alkyl or aryl optionally at least monosubstituted; and $X^7$ is alkyl; and provided that when R is H and $R^1$ is

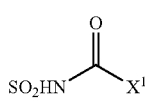

$X^1$ is an alkyl with at least two carbon atoms;

—$OX^2$; or an aryl optionally at least monosubstituted; and $X^2$ is alkyl;

and their pharmaceutically acceptable salts, their stereoisomeric forms, preferably their pure enantiomeric or diastereomeric forms, and their racemate forms, or a mixture thereof in any mixture ratio, and their N-oxides and the corresponding solvates or hydrates.

In another embodiment of the first aspect of the invention, the pyrazoline derivative of formula (I) is a derivative in which when $R^1$ is H; and R is

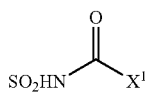

$X^1$ is an alkyl substituted by at least one group selected from halogen, hydroxy, amine, carboxy, carboxyalkyl and acylamine. Preferably, $X^1$ is selected from:
—CH$_2$OH;
—(CH$_2$)$_4$—Br;

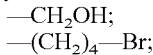

—CH(NH$_2$)—CH$_3$;
—CH(NH$_2$)—(CH$_2$)$_2$—COOH;
—CH(NHBOC)—(CH$_2$)$_4$(NHBOC);
—CH$_2$CH$_2$COOH;
—CH$_2$OCOCH$_3$;
(NHBOC=at-butoxycarbonylamine).

In another embodiment of the first aspect of the invention, the pyrazoline derivative is a derivative in which when
$R^1$ is H; and
R is

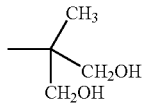

$X^1$ is a cycloalkyl, preferably cyclohexyl.

In yet another embodiment of the first aspect of the invention, the pyrazoline derivative of formula (I) is a derivative in which when
$R^1$ is H; and
R is

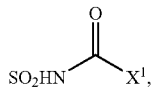

$X^1$ is a —OX$^2$ group, $X^2$ being an alkyl group. Preferably, $X^2$ is selected from methyl, ethyl, propyl, isopropyl, butyl, isobutyl and neopentyl.

In another embodiment of the first aspect of the invention, the pyrazoline derivative of formula (I) is a derivative in which when
$R^1$ is H; and
R is

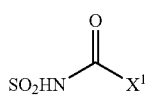

$X^1$ is

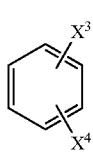

and
$X^3$ and $X^4$ can be the same as or different from each other and are selected from H; an aryl group optionally at least monosubstituted; haloalkyl group; alcoxyl group; halogen; amine; nitro; cyano; —CO$_2$X$^5$; —COX$^6$ and —SO$_2$X$^7$;
$X^5$ is hydrogen or alkyl;
$X^6$ is alkyl or aryl optionally monosubstituted; and
$X^7$ is alkyl.

Preferably $X^3$ and $X^4$ are selected from H, fluor, nitro, CN, chloromethyl, trifluoromethyl, methoxyl, phenyl; $X^5$ is H or methyl; $X^6$ is methyl or phenyl; and $X^7$ is methyl.

In another embodiment of the first aspect of the invention, the pyrazoline derivative of formula (I) is a derivative in which when
R is H; and
$R^1$ is

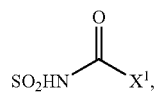

$X^1$ is an alkyl with at least two carbon atoms. Preferably, $X^1$ is selected from ethyl and tert-butyl.

In yet another embodiment of the first aspect of the invention, the pyrazoline derivative of formula (I) is a derivative in which when
R is H; and
$R^1$ is

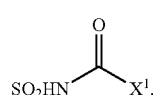

$X^1$ is —OX$^2$, $X^2$ being an alkyl group. Preferably, $X^2$ is selected from methyl, ethyl, propyl, isopropyl, butyl and neopentyl.

In still yet another embodiment of the first aspect of the invention, the pyrazoline derivative of formula (I) is a derivative in which when
R is H, and
$R^1$ is

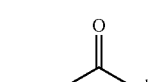

$X^1$ is an aryl optionally at least monosubstituted, preferably a phenyl substituted by a trifluoromethyl.

Preferably, the pyrazoline derivative of formula (I) is selected from the group consisting of:
*N-Methoxycarbonyl-4-(4,5-dihydro-5-phenyl-3-trifluoromethyl-pyrazole-1-yl)-benzenesulphonamide;
*N-((2-Acethyloxi)acetyl)-4-(4,5-dihydro-5-phenyl-3-trifluoromethyl-pyrazole-1-yl)-benzenesulphonamide;
*N-(2-Hydroxyacetyl)-4-(4,5-dihydro-5-phenyl-3-trifluoromethyl-pyrazole-1-yl)-benzenesulphonamide;
*N-Ethyloxicarbonyl-4-(4,5-dihydro-5-phenyl-3-trifluoromethyl-pyrazole-1-yl)-benzenesulphonamide;
*N-Propyloxicarbonyl-4-(4,5-dihydro-5-phenyl-3-trifluoromethyl-pyrazole-1-yl)-benzenesulphonamide;
*N-Isopropyloxicarbonyl-4-(4,5-dihydro-5-phenyl-3-trifluoromethyl-pyrazole-1-yl)-benzenesulphonamide;
*4-oxo-4-[4-(4,5-dihydro-5-phenyl-3-trifluoromethyl-pyrazole-1-yl)-benzenesulphonylamine] butyric acid;

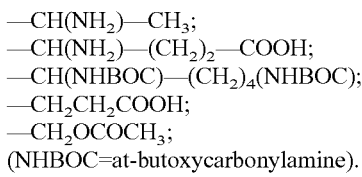
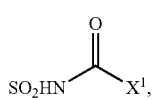

*N-Butyloxicarbonyl-4-(4,5-dihydro-5-phenyl-3-trifluoromethyl-pyrazole-1-yl)-benzenesulphonamide;
*N-(2-Methylpropionyloxicarbonyl)-4-(4,5-dihydro-5-phenyl-3-trifluoromethyl-pyrazole-1-yl)-benzenesulphonamide;
*N-(5-Bromopentanoyl)-4-(4,5-dihydro-5-phenyl-3-trifluoromethyl-pyrazole-1-yl)-benzenesulphonamide;
*N-(2,2-Dimethylpropyloxicarbonyl)-4-(4,5-dihydro-5-phenyl-3-trifluoromethyl-pyrazole-1-yl)-benzenesulphonamide;
*N-(2-Hydroxymethyl-2-methyl-3-hydroxypropionyl)-4-(4,5-dihydro-5-phenyl-3-trifluoromethyl-pyrazole-1-yl)-benzenesulphonamide;
*N-(Cyclohexanocarbonyl)-4-(4,5-dihydro-5-phenyl-3-trifluoromethyl-pyrazole-1-yl)-benzenesulphonamide;
*N-(2-Aminepropionyl)-4-(4,5-dihydro-5-phenyl-3-trifluoromethyl-pyrazole-1-yl)-benzenesulphonamide;
*4-Amine-5-oxo-5-[4-(4,5-dihydro-5-phenyl-3-tri-fluoromethyl-pyrazole-1-yl)-benzenesulphonylamine] pentanoic acid;
*N-[(2,6-diterbutoxycarbonylamine)hexanoyl]-4-(4,5-dihydro-5-phenyl-3-trifluoromethyl-pyrazole-1-yl)-benzenesulphonamide;
*N-Benzoyl-4-(4,5-dihydro-5-phenyl-3-trifluoromethyl-pyrazole-1-yl)-benzenesulphonamide;
*N-(Biphenyl-4-carbonyl)-4-(4,5-dihydro-5-phenyl-3-trifluoromethyl-pyrazole-1-yl)-benzenesulphonamide;
*N-(3-Chloromethylbenzoyl)-4-(4,5-dihydro-5-phenyl-3-trifluoromethyl-pyrazole-1-yl)-benzenesulphonamide;
*N-(4-Methoxybenzoyl)-4-(4,5-dihydro-5-phenyl-3-trifluoromethyl-pyrazole-1-yl)-benzenesulphonamide;
*N-(4-Cyanobenzoyl)-4-(4,5-dihydro-5-phenyl-3-trifluoromethyl-pyrazole-1-yl)-benzenesulphonamide;
*N-(4-Trifluoromethylbenzoyl)-4-(4,5-dihydro-5-phenyl-3-trifluoromethyl-pyrazole-1-yl)-benzenesulphonamide;
*N-(4-Fluoro-2-trifluoromethylbenzoyl)-4-(4,5-dihydro-5-phenyl-3-trifluoromethyl-pyrazole-1-yl)-benzenesulphonamide;
*N-(4-Nitrobenzoyl)-4-(4,5-dihydro-5-phenyl-3-trifluoromethyl-pyrazole-1-yl)-benzenesulphonamide;
*4-[4-(4,5-dihydro-5-phenyl-3-trifluoromethyl-pyrazole-1-yl)-benzenesulphonylamine] benzoic acid methylic ester;
*4-[4-(4,5-dihydro-5-phenyl-3-trifluoromethyl-pyrazole-1-yl)-benzenesulphonylaminecarbonyl] benzoic acid;
*N-(2-Trifluoromethylbenzoyl)-4-(4,5-dihydro-5-phenyl-3-trifluoromethyl-pyrazole-1-yl)-benzenesulphonamide;
*N-(4-Metansulphonylbenzoyl)-4-(4,5-dihydro-5-phenyl-3-trifluoromethyl-pyrazole-1-yl)-benzenesulphonamide;
*N-(4-Acetyl-benzoyl)-4-(4,5-dihydro-5-phenyl-3-trifluoromethyl-pyrazole-1-yl)-benzenesulphonamide;
*N-(4-Benzoyl-benzoyl)-4-(4,5-dihydro-5-phenyl-3-trifluoromethyl-pyrazole-1-yl)-benzenesulphonamide;
*N-Methoxycarbonyl-4-(4,5-dihydro-1-phenyl-3-trifluoromethyl-1H-pyrazole-5-yl)benzenesulphonamide;
*N-Propionyl-4-(4,5-dihydro-1-phenyl-3-trifluoromethyl-1H-pyrazole-5-yl)benzenesulphonamide;
*N-Ethoxycarbonyl-4-(4,5-dihydro-1-phenyl-3-trifluoromethyl-1H-pyrazole-5-yl)benzenesulphonamide;
*N-Propoxycarbonyl-4-(4,5-dihydro-1-phenyl-3-trifluoromethyl-1H-pyrazole-5-yl)benzenesulphonamide;
*N-Isopropoxycarbonyl-4-(4,5-dihydro-1-phenyl-3-trifluoromethyl-1H-pyrazole-5-yl)benzenesulphonamide;
*N-(2,2-Dimethyl)propionyl-4-(4,5-dihydro-1-phenyl-3-trifluoromethyl-1H-pyrazole-5-yl)benzenesulphonamide;
*N-Butoxycarbonyl-4-(4,5-dihydro-1-phenyl-3-trifluoromethyl-1H-pyrazole-5-yl)benzenesulphonamide;
*N-(2,2-Dimethyl)propoxycarbonyl-4-(4,5-dihydro-1-phenyl-3-trifluoromethyl-1H-pyrazole-5-yl)benzenesulphonamide;
*N-(4-Trifluoromethyl)benzoil-4-(4,5-dihydro-1-phenyl-3-trifluoromethyl-1H-pyrazole-5-yl)benzenesulphonamide;

and their pharmaceutically acceptable salts, their stereoisomeric forms, preferably their pure enantiomeric or diastereomeric forms and their racemate forms, or a mixture thereof in any mixture ratio, and their N-oxides and the corresponding solvates or hydrates.

In a preferred embodiment, said pyrazoline derivative is in the form of a salt, preferably in the form of a sodium salt.

Surprisingly, the inventors of this invention have found that the compounds of general formula (I) have improved solubility properties in an aqueous medium at physiologically tolerated pH. Said properties permit these compounds to be administered by parenteral injection, in particular by subcutaneous, intramuscular, intraperitoneal or endovenous administration.

This advantageous aspect means a substantial improvement in the field of anti-inflammatories and analgesics, since these compounds are soluble they can be administered by injection or infusion and exert their action rapidly, unlike most compounds already known in the state of the art, which are characterised by being administered orally (said compounds requiring a longer time to exert their therapeutic action).

Therefore, under a second aspect, this invention relates to a pyrazoline derivative of general formula (I), in accordance with the first aspect, for use as a medicament.

Preferably, said pyrazoline derivative is in the form of a salt, more preferably in the form of a sodium salt.

Under a third aspect, the invention relates to a pharmaceutical composition which includes at least one pyrazoline derivative in accordance with the first aspect of the invention, for use as a medicament.

Preferably, said pharmaceutical composition includes at least one pyrazoline derivative in accordance with the first aspect of the invention in a therapeutically active amount and at least one pharmaceutically acceptable diluent or adjuvant, for use as an anti-inflammatory.

In another embodiment of the third aspect of the invention, said pharmaceutical composition includes at least one pyrazoline derivative in accordance with the first aspect of the invention in a therapeutically active amount and at least one pharmaceutically acceptable diluent or adjuvant, for use as an analgesic.

Preferably, said pyrazoline derivative is present in said pharmaceutical composition in the form of a salt, still more preferably in the form of a sodium salt of said pyrazoline derivative.

Under a fourth aspect, this invention relates to the use of a pyrazoline derivative in accordance with the first aspect of this invention for the manufacture of a medicament for the treatment of inflammation in an animal, as for example a post-traumatic inflammation, a post-surgical inflammation, rheumatoid arthritis, an ocular inflammation, etc.

Under a fifth aspect, this invention relates to the use of a pyrazoline derivative in accordance with the first aspect of the invention for the manufacture of a medicament for the treatment of pain in an animal, as for example post-traumatic pain, post-surgical or osteoarthritic pain; ocular pain; neuropathic pain and allodinia.

In a preferred embodiment, said pyrazoline derivative is in the form of a salt, more preferably in the form of a sodium salt.

Preferably, said animal is a mammal, and more preferably a human.

In yet another embodiment of the fifth aspect of the invention, said medicament is administered in the form of a parenteral injection or infusion, preferably subcutaneously, intramuscularly, intraperitoneally or endovenously.

In yet another embodiment of the sixth aspect of the invention, said medicament is administered in the form of a collyrium.

The derivatives of pyrazoline can be obtained in accordance with the synthesis procedures illustrated in Schemes 1 and 2:

Scheme 1:

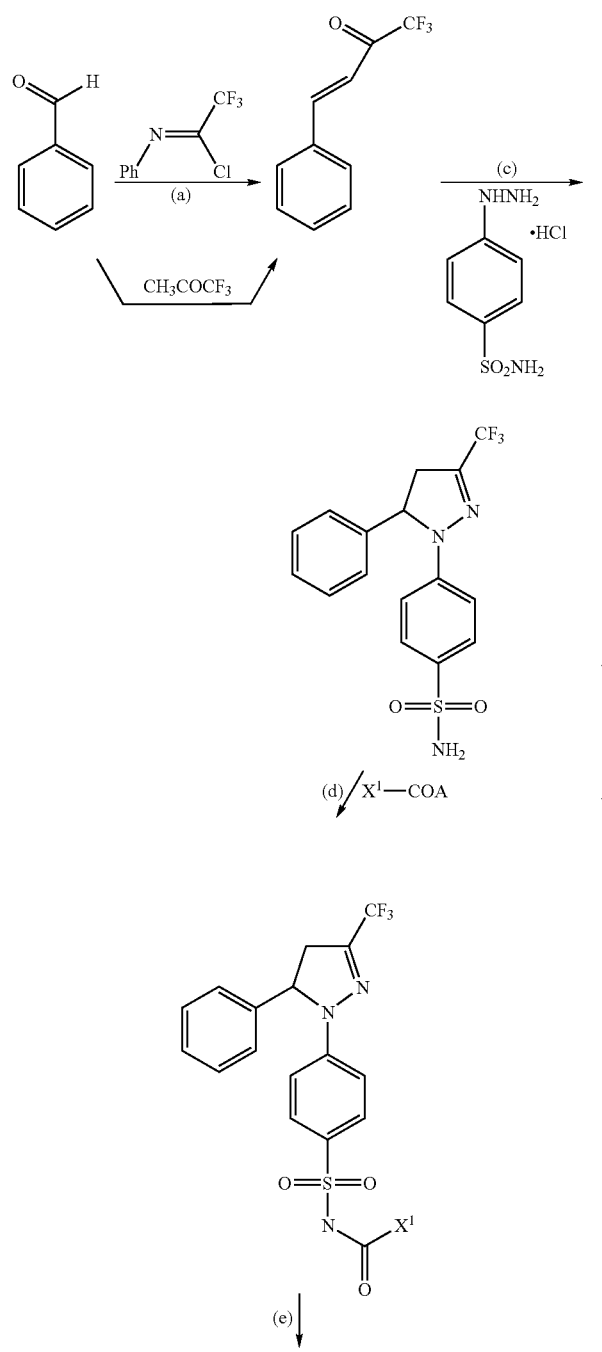

Scheme 2:

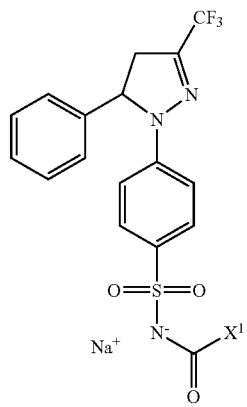

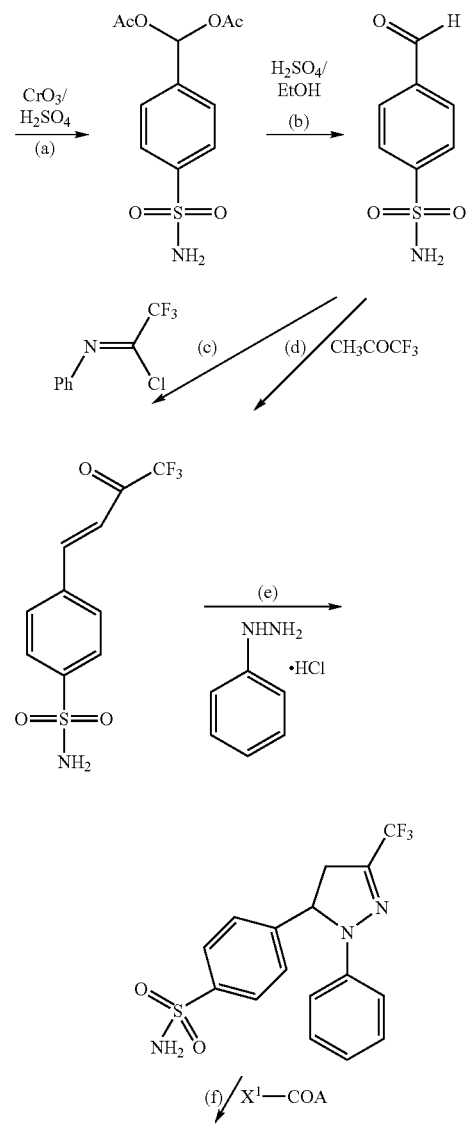

-continued

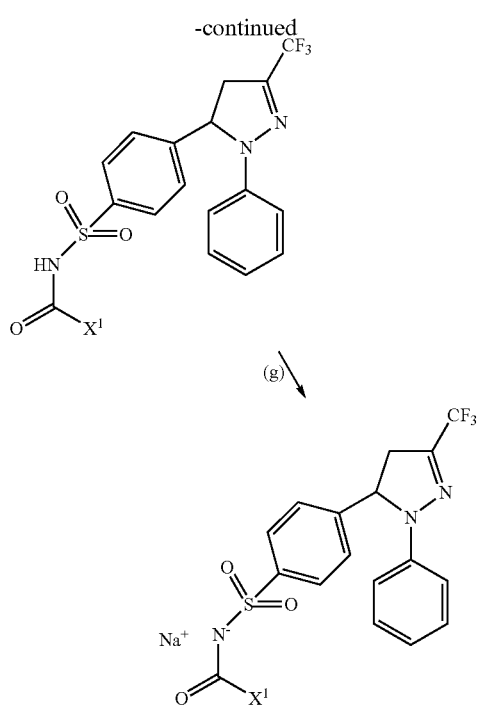

(g)

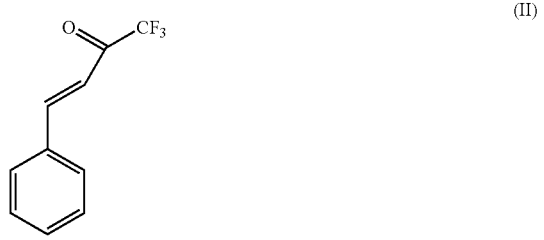

In order to obtain the compounds of general formula (I), in which R means —SO$_2$NH—CO—X$^1$ and R$^1$ is hydrogen, the synthetic route shown in Scheme 1 is followed.

The compound of formula (II):

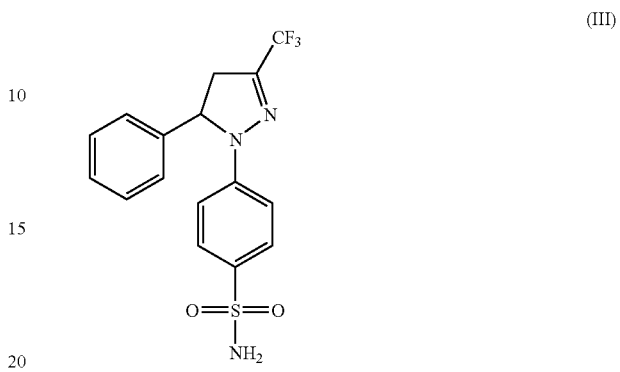

can be obtained in various ways very well-known by those skilled in the art. In particular, it can be prepared through two possible steps of synthesis:

(a) by reaction of the benzaldehyde with N-phenyltrifluoroacetimidoyl chloride, in the presence of a dialkyl phosphonate, such as diethylmethyl phosphonate, and a strong organic base, such as lithium diisopropylamide (LDA), or by Wittig reaction with trifluoroacetylmethylenetriphenylphosphorane and a base such as sodium carbonate or potassium carbonate. N-phenyltrifluoroacetimidoyl chloride is prepared as described by K. Tamura et al., in J. Org. Chem., 58(1), 32-35. (1993). The reaction is carried out in a suitable solvent, such as, for example, dichloromethane, chloroform or benzene, or an ether such as, for example, tetrahydrofuran, ethyl ether, dimethoxyethane or dioxane, or mixtures thereof. The temperatures can range from −70° C. to the reflux temperature of the solvent, and the reaction can last from fifteen minutes to several hours.

(b) by aldolic condensation reaction between the benzaldehyde and the trifluoromethylketone. The reaction is carried out in a suitable solvent, such as tetrahydrofuran, dimethoxyethane, dimethylsulphoxide, dimethylformamide, or mixtures thereof, in the presence, or not, of water. The catalyst used for the reaction can be a base such as, for example, piperidine, potassium hydroxide, sodium hydroxide or lithium hydroxide, or an acid such as, for example, acetic acid. Other catalysts can also be used, such as zinc nitrate (see P. T. Buonona et al., Tetrahedron Lett., 4009-4012. (1995))

The compound of formula (III):

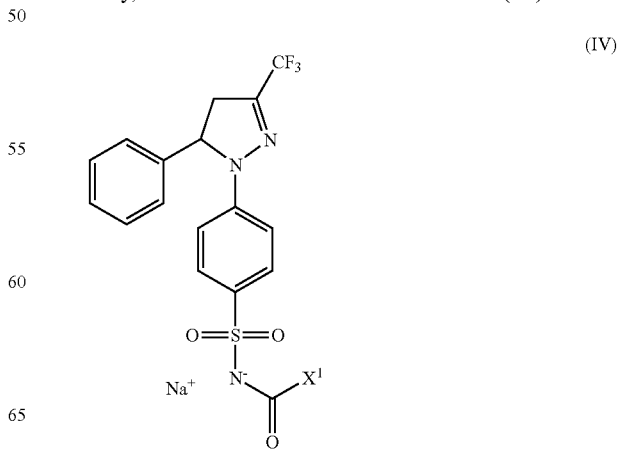

is obtained by condensation of the compound of formula (II) with 4-aminesulphonylphenylhidrazine hydrochloride. The reaction is carried out in the presence of a suitable solvent, which can be an alcohol, such as methanol, ethanol or isopropanol, an ether such as dioxane or tetrahydrofuran, or mixtures thereof, and is carried out in an acidic medium, which can be organic such as acetic acid, or inorganic such as hydrochloric acid, or in a basic medium such as, for example, piperidine, sodium hydroxide, potassium hydroxide, sodium methoxide or sodium ethoxide, or a mixture thereof. The acid or basic medium can also act as a solvent. The reaction temperature can range from room temperature to the reflux temperature of the solvent, and the reaction time can range from several hours to several days.

The compound of formula (III) can react with a compound of general formula X$^1$CO-A to give rise to the compounds of general formula (I), (see N. Ishizuka et al., Synthesis, 6. 784-788, 2000), wherein X$^1$ has the same meaning stated above for R$^1$=H and R=—SO$_2$NH—CO—X$^1$· and A can mean a halogen, mainly chlorine or bromine, so that the compound X$^1$CO-A means an acid chloride or bromide or a chloroformiate, or A means —OCOX$^1$, so that the compound X$^1$CO-A means an anhydride.

The compounds of general formula X$^1$CO-A are, in general, commercially available, and they may also be prepared by various synthetic routes very well-known to those skilled in the art.

Finally, if it is wished to obtain a sodium salt (IV)

it can be prepared, for example, by reacting the compounds of general formula (I) with a base such as sodium bicarbonate, sodium carbonate or sodium hydroxide.

The compounds of general formula (I) in which R means hydrogen and $R^1$ means —$SO_2NH$—CO—$X^1$ are prepared in accordance with the general synthetic route shown in Scheme 2. The starting product is p-toluenesulphonamide which, as shown in step (a) of Scheme 2, is oxidised with chromium trioxide in an acetic anhydride and sulphuric acid medium to give rise to the corresponding diacetate, which is hydrolised directly to 4-formyl benzenesulphonamide, in acidic medium, without being purified (see: S. V. Lieberman and R. Connor, Organic Synthesis, Col. Vol. II, p. 441). This aldehyde (V):

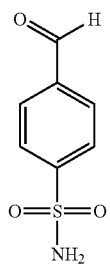

(V)

is converted into 4-(4,4,4-trifluoro-3-oxo-2-butenyl)-benzenesulphonamide (VI):

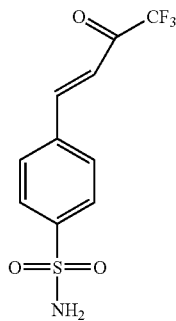

(VI)

through synthetic steps (c) or (d) of Scheme 2, which are identical, respectively, to synthetic steps (a) and (b) of Scheme 1 described above (see: J. Chem. Soc. Perkin Trans I, 741-742. (1995).

By condensation of compound (VI) with the hydrochloride of a phenylhydrazine (step (e) of Scheme 2) a new pyrazoline derivative (VII) is obtained:

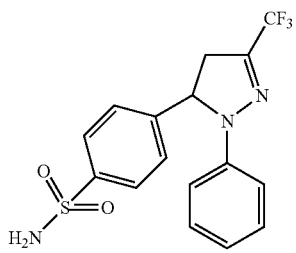

(VII)

which is in turn converted into the corresponding compounds of general formula (I) by reaction with the compound of general formula (VIII):

$X^1$CO-A        (VIII)

wherein $X^1$ has the meaning stated above for the case when R=H and $R^1$ is

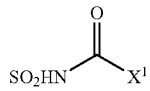

and A has the meaning stated above.

The compounds of general formula $X^1$CO-A are in general and, as noted above, commercially available, and they can also be prepared using various synthetic routes very well known by those skilled in the art.

In an analogous way to that stated previously, these compounds of general formula (I) can also be converted into their corresponding sodium salts.

In a preferred embodiment, said pyrazoline derivative is in the form of a salt, based on the acid hydrogen existing in the group:

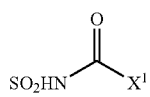

preferably in the form of a sodium salt.

It is also possible to prepare a salt based on any other acid group present in the molecule as substituent in any of the possible positions indicated herein earlier, in which case a disalt is obtained. Preferably also a sodium salt.

In an analogous way, a salt can also be prepared from a basic group, for example amine, which is present in any of the possible positions according to the possible substituents defined previously. In these cases, the salt can be prepared by using an inorganic acid, such as hydrochloric acid, hydrobromic acid, trifluoroacetic acid and the like; or using an organic acid, such as, for example, maleic acid, fumaric acid, citric acid, oxalic acid or the like.

The new compounds of general formula (I) object of this invention present at least one asymmetric atom carbon, and their stereoisomeric forms can therefore be prepared, preferably their pure enantiomeric or diastereomeric forms, and their racemate forms, or a mixture thereof in any mixture ratio, and their N-oxides and the corresponding solvates or hydrates. The racemates of the compounds of general formula (I) can be resolved into their optical isomers by means of conventional procedures such as separation by chromatography with chiral stationary phase, or by means of fractionated crystallisation of their diastereoisomeric salts, which can be prepared by reaction of the compounds of general formula (I) with enantiomerically pure acids or bases. In a similar way, they can also be obtained by enantioselective synthesis using enantiomerically pure chiral precursors.

Next, the following examples are enclosed by way of non-restrictive illustration.

EXAMPLES

Example 1

Preparation of the sodium salt of N-methoxycarbonyl-4-(4,5-dihydro-1-phenyl-3-trifluoromethyl-1H-pyrazole-5-yl) benzenesulphonamide
(Compound 31 of Table 1)

(a) and (b) 4-Formil benzenesulphonamide

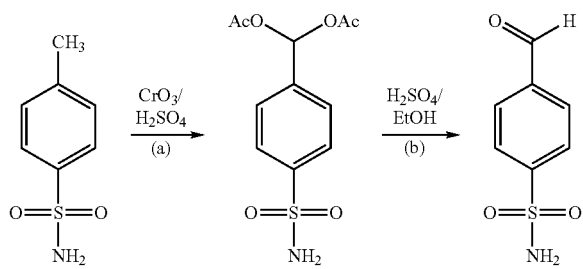

Acetic anhydride (400 ml) is placed in a 1000 ml flask, cooled to −10° C., CrO$_3$ (70 g, 0.7 moles) is added and stirred for 1 h at 0° C.

In another flask p-toluenesulphonamide (40 g, 234 mmoles) is suspended in acetic anhydride (350 ml), cooled to −10° C. and H$_2$SO$_4$ (60 ml) is added dropwise and slowly, since the reaction is quite exothermic. The solid is dissolved entirely. It is left for 15 min at 0° C. and the solution of the oxidising mixture, prepared independently as indicated above, is added to it. Once the addition is finished it is stirred for 2.5 h at 0° C. It is then poured onto ice-water (approximate ratio of 7:1, 4 liters) and it is stirred overnight. The resulting solution is extracted with AcOEt, the organic solution is washed with water, dried over sodium sulphate, filtered and evaporated to dryness.

To the resulting pasty mixture, ethanol (130 ml), water (40 ml) and H$_2$SO$_4$ (8 ml) are added, and it is heated at reflux for 2.5 h. It is cooled, solvent is eliminated in a rotavapor and the residue is separated between AcOEt and water. The organic phase is washed with a 5% potassium carbonate solution and water. Once the organic solution is dried and evaporated, there remain 13.4 g (31%) of crude, cream-coloured solid, which is used without purifying in the next stage.

IR (KBr, cm$^{-1}$): 3357, 3244, 1701, 1337, 1172

$^1$H NMR (d$_6$-DMSO, δ ppm): 7.57 (s, 2H), 8.0 (d, J=8.2 Hz, 2H), 8.1 (d, J=8.2 Hz, 2H), 10.1 (s, 1H)

(c) 4-(4,4,4-trifluoro-3-oxo-2-butenyl)-benzenesulphonamide

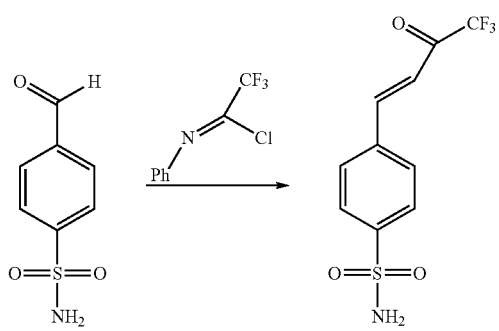

200 ml of anhydrous THF are placed into a flask with a dry and inert atmosphere, it is cooled to −78° C. and 72.4 ml of LDA 2M solution in THF/n-heptane is added at a speed that allows the temperature to be kept below −65° C. Diethylmethylphosphonate (10.57 ml, 72.4 mmoles) dissolved in 60 ml of THF is then added rapidly dropwise and it is stirred for 30 minutes at −78° C. The N-phenyltrifluoroacetimidoyl chloride (15.03 g, 72.4 mmoles) obtained in the preceding reaction, dissolved in 40 ml of THF, is added dropwise and the stirring is continued under the same conditions for 2 hours. The solution of 4-formyl benzenesulphonamide (13.4 g, 72.4 mmoles) in 100 ml of THF is added, the cold bath is removed and the temperature is left to rise to room temperature. It is stirred overnight under these conditions.

Next morning 150 ml of HCl 2N are added and stirring is continued for 24 hours. The THF is eliminated in a rotavapor and the resulting aqueous solution is extracted with AcOEt (2×200 ml), washed with 5% NaHCO$_3$ solution and with saturated solution of NaCl, dried over sodium sulphate, filtered and the solvent evaporated in a rotavapor. 7.86 g (40%) of crude product is obtained, which is purified by column chromatography, eluting with chloroform and chloroform-MeOH 95:5, yielding a 5.4 g fraction of pure product and another 2.13 g fraction of slightly unpurified product in the form of cream-coloured solid (total yield 37%).

$^1$H NMR (d$_6$-DMSO, δ ppm) 7.5 (m, 3H), 7.9 (d, J=8.3 Hz, 2H), 8.05 (s, 1H), 8.1 (d, J=8.3 Hz, 2H)

(e) 5-(4-aminesulphonylphenyl)-4,5-dihydro-1-phenyl-3-trifluoro-methyl-1H-pyrazole

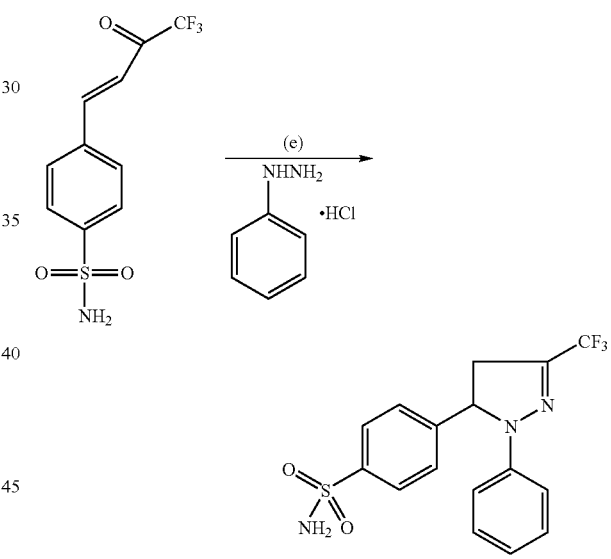

4-(4,4,4-trifluoro-3-oxo-2-en)-benzenesulphonamide (5.4 g, 19.28 mmoles), phenylhydrazine hydrochloride (2.79 g, 19.28 mmoles) and glacial acetic acid (150 ml) are placed in a flask with an inert atmosphere. It is refluxed overnight and next morning it is poured onto water-ice (≈250 ml), stirred for a few minutes and the resulting solid filtered and washed with water. 2.23 g are obtained.

The filtered waters are extracted with AcOEt, washed with water, dried over sodium sulphate, filtered and evaporated, yielding an impure product which is purified by column chromatography and subsequent crystallisation from ethanol. A further 0.35 g are obtained and added to the filtered product to yield 2.58 g (36%) of a beige-coloured solid product m.p.=162-167° C.

IR (KBr, cm$^{-1}$): 3345, 3259, 1598, 1503, 1330, 1147

$^1$H NMR (d$_6$-DMSO, δ ppm): 3.0 (dd, J=12.1 and 17.7 Hz, 1H), 3.85 (m, 1H), 5.8 (m, 1H), 6.9 (t, J=7.2 Hz, 1H), 6.9 (d, J=8.0 Hz, 2H), 7.2 (m, 2H), 7.4(s br, 2H), 7.45 (d, J=8.2 Hz, 2H), 7.8 (d, J=8.2 Hz, 2H)

(f) and (g) Sodium salt of N-methoxycarbonyl-4-(4,5-dihydro-1-phenyl-3-trifluoromethyl-1H-pyrazole-5-yl) benzenesulphonamide

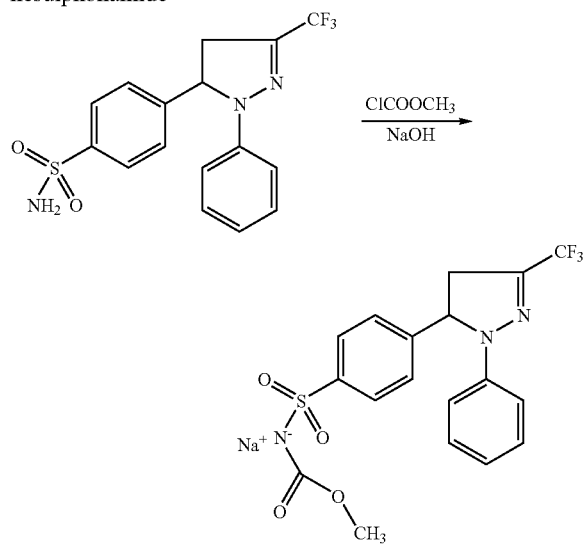

5-(4-aminesulphonylphenyl)-4,5-dihydro-1-phenyl-3-trifluoromethyl-1H-pyrazole (1.6 g, 4.33 mmoles), dissolved in methylene chloride (65 ml), is placed in a flask with inert atmosphere, cooled with ice and, then, powdered KOH 85% (0.91 g, 13.85 mmoles) is added all at once. The mixture is stirred at 0° C. for 30 minutes and methyl chloroformiate (0.5 ml, 6.5 mmoles) is then added. It is left at room temperature overnight (approximately 19 h) under stirring. The solvent is evaporated in a rotavapor and AcOEt and HCl 0.1N are added. The organic phase is washed with water, and then twice with NaOH 10%. The basic aqueous solution is washed again with AcOEt and the combined organic phases washed with NaCl-saturated solution, dried over sodium sulphate, filtered and evaporated to dryness. A crude sodium salt is obtained, which is crystallised from MeOH-ethylic ether, yielding 1.5 g (77%) of white solid product with m.p.=244-247° C.

IR (KBr, cm$^{-1}$): 1640, 1600, 1308, 1123, 1075

$^1$H NMR (d$_6$-DMSO, δ ppm): 2.9 (dd, J=6.5 and 18.2 Hz, 1H), 3.2 (s, 3H), 3.8 (dd, J=18.2 and 12.8 Hz, 1H), 5.7 (dd, J=6.5 and 12.8 Hz, 1H), 6.8 (t, J=7.3 Hz, 1H), 6.95 (d, J=7.7 Hz, 2H), 7.15-7.25 (m, 4H), 7.7 (d, J=8.2 Hz, 2H)

Example 2

Preparation of N-(2-hydroxyacetyl)-4-(4,5-dihydro-5-phenyl-3-trifluoromethyl-pyrazole-1-yl) (Compound 3 of Table 1)

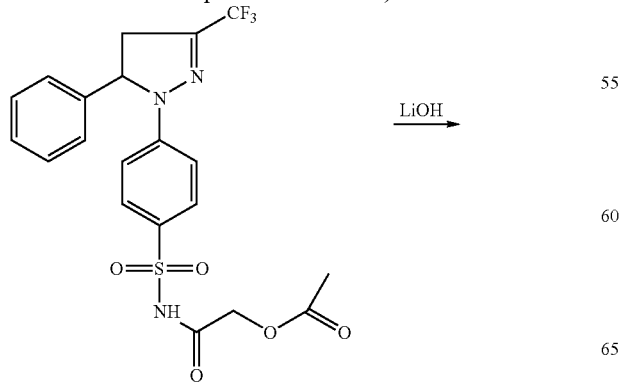

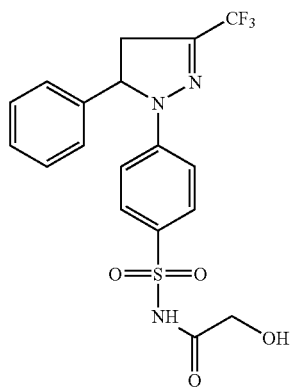

An inert nitrogen-atmosphere reactor, containing a solution of N-((2-acethyloxi)acetyl)-4-(4,5-dihydro-5-phenyl-3-trifluoromethyl-pyrazole-1-yl)-benzenesulphonamide (compound 2 of Table 1, prepared in a similar way to that described in example 1; 1.2 g, 2.56 mmoles) in a mixture of tetrahydrofuran (40 ml) and water (15 ml), is cooled to 0° C., and to this is added monohydrated lithium hydroxide (0.16 g, 3.84 mmoles). This is stirred at room temperature overnight. The tetrahydrofuran is evaporated in a rotavapor and the resulting aqueous solution is acidified with hydrochloric acid and extracted with ethyl acetate, washed with water, dried over sodium sulphate and eliminated in a rotavapor. 0.86 g (yield 79%) of yellowish solid with m.p.=138-140° C. is obtained.

IR (KBr, cm$^{-1}$): 3448, 1719, 1593, 1332, 1136, 1067

$^1$H NMR (CDCl$_3$. δ ppm): 2.6 (s bd, 1H), 3.0 (dd, J=6.8 and 18.3 Hz, 1H), 3.7 (dd, J=12.6 and 18.3 Hz, 1H), 4.1 (s, 2H), 5.5 (dd, J=6.8 and 12.6 Hz, 1H), 7.05 (d, J=9.1 Hz, 2H), 7.2-7.4 (m, 5H), 7.9 (d, J=9.1 Hz, 2H), 9.0 (s bd, 1H)

Example 3

Preparation of 4-oxo-4-[4-(4,5-dihydro-5-phenyl-3-trifluoromethyl-pyrazole-1-yl)-benzenesulphonyl-amine] butyric acid (Compound 7 of Table 1)

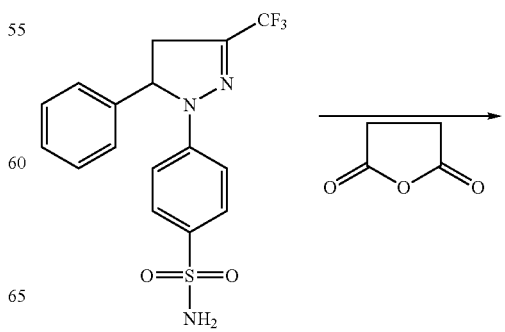

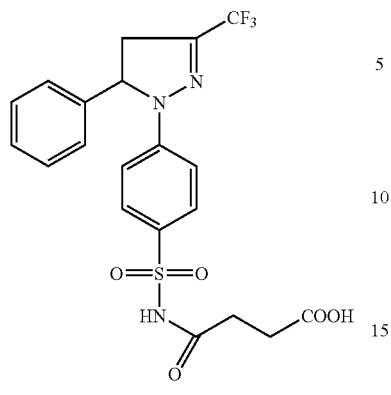

A solution of 4-(4,5-dihydro-5-phenyl-3-trifluoromethyl-pyrazole-1-yl) benzenesulphonamide (0.1 g, 0.27 mmoles), succinic anhydride (54 mg, 0.54 mmoles), dimethylaminepyridine (16 mg, 0.14 mmoles) and triethylamine (0.045 ml, 0.32 mmoles) in anhydrous tetrahydrofuran is heated at reflux for 20 hours in an inert nitrogen atmosphere. It is cooled and the solvent eliminated in a rotavapor. The resulting aqueous solution is acidified with hydrochloric acid and extracted with ethyl acetate. The organic solution is washed with a saturated solution of sodium chloride and with sodium bicarbonate solution. The basic aqueous solution is acidified with hydrochloric acid, the white solid precipitated is filtered and dried. 65 mg (yield 52%) of 4-oxo-4-[4-(4,5-dihydro-5-phenyl-3-trifluoromethyl-pyrazole-1-yl)-benzenesulphonylamine] butyric acid is obtained in the form of an amorphous solid.

$^1$H-NMR (MeOH-$d_4$, δ ppm): 2.5 (s, 4H), 3.1 (dd, J=6.3 and 18.3 Hz, 1H), 3.9 (dd, J=12.8 and 18.3 Hz, 1H), 5.8 (dd, J=12.8 and 6.3 Hz, 1H), 7.2 (d, J=9.0 Hz, 2H), 7.3-7.5 (m, 5H), Example 4

Preparation of the sodium salt of N-(Cyclohexanocarbonyl)-4-(4,5-dihydro-5-phenyl-3-trifluoromethyl-pyrazole-1-yl)-benzenesulphonamide (Compound 13 of Table 1)

(a) N-(Cyclohexanocarbonyl)-4-(4,5-dihydro-5-phenyl-3-trifluoromethyl-pyrazole-1-yl)-benzenesulphonamide In a flask with inert nitrogen atmosphere 4-(4,5-dihydro-5-phenyl-3-trifluoromethyl-pyrazole-1-yl) benzenesulphonamide (0.5 g, 1.35 mmoles) and triethylamine (0.94 ml) are dissolved in dichloromethane. This is cooled in an ice bath and cyclohexanecarboxylic acid chloride (0.22 ml, 1.63 mmoles) is added to it. The cold bath is removed and it is then heated at reflux for 2 hours. It is cooled, water is added and the organic phase is washed with a saturated solution of sodium chloride, dried over sodium sulphate, filtered and evaporated to dryness. The resulting residue is purified by silica gel column chromatography (eluent: ethyl acetate/petroleum ether 4/6 to 7/3). 0.43 g (yield 66%) of N-(cyclohexanocarbonyl)-4-(4,5-dihydro-5-phenyl-3-trifluoromethyl-pyrazole-1-yl) benzenesulphonamide is obtained in the form of an amorphous white solid.

IR (KBr, cm$^{-1}$): 3256, 1719, 1593, 1331, 1170, 1089, 1067

$^1$H-NMR (CDCl$_3$, δ ppm): 1.25 (m, 5H), 1.7 (m, 5H), 2.1 (m, 1H), 3.05 (dd, J=6.8 and 18.1 Hz, 1H), 3.7 (dd, J=12.6 and 18.1 Hz, 1H), 5.4 (dd, J=6.8 and 12.6 Hz, 1H), 7.0 (d, J=8.8 Hz, 2H), 7.2-7.4 (m, 5H), 7.8 (d, J=8.8 Hz, 2H), 8.25 (s, 1H)

(b) Sodium salt of N-(cyclohexanocarbonyl)-4-(4,5-dihydro-5-phenyl-3-trifluoromethyl-pyrazole-1-yl)-benzenesulphonamide

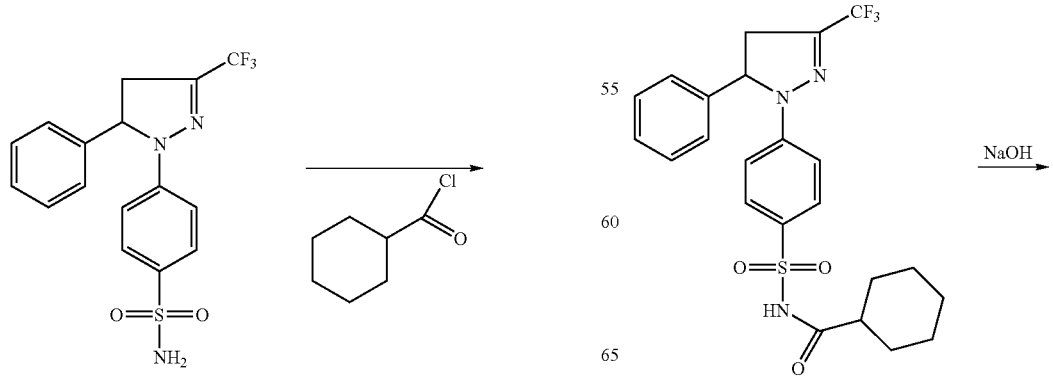

-continued

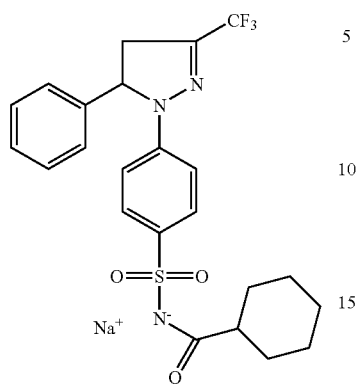

N-(cyclohexanecarbonyl)-4-(4,5-dihydro-5-phenyl-3-trifluoromethyl-pyrazole-1-yl) benzenesulphonamide (0.43 g, 0.9 mmoles), dissolved in methanol (10 ml), is ice cooled and the stoichiometric amount of an aqueous solution of sodium hydroxide 0.1N (0.9 mmoles) is added. The solvent is eliminated in a rotavapor and 0.44 g (yield 98%) of the corresponding sodium salt is obtained in form of a yellowish solid with m.p.>280° C.

$^1$H-NMR (MeOH-d$_4$, δ ppm): 1.25 (m, 5H), 1.7 (m, 5H), 2.1 (m, 1H), 2.9 (dd, J=6.9 and 18.3 Hz, 1H), 3.8 (dd, J=12.5 and 18.3 Hz, 1H), 5.6 (dd, J=6.9 and 12.5 Hz, 1H), 7.0 (d, J=8.8 Hz, 2H), 7.2-7.4 (m, 5H), 7.7 (d, J=8.8 Hz, 2H)

Example 5

Preparation of N-(2-aminepropionyl)-4-(4,5-dihydro-5-phenyl-3-trifluoromethyl-pyrazole-1-yl)-benzenesulphonamide (Compound 14 of Table 1)

a) {1-methyl-2-oxo-2-[4-(5-phenyl-3-trifluoromethyl-4,5-dihydro-pyrazole-1-yl)-benzenesulphonylamine]-ethyl}-carbamic acid t-butylic ester

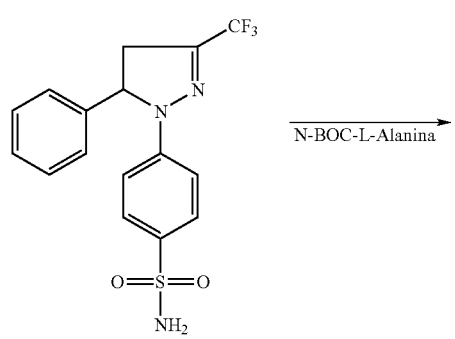

-continued

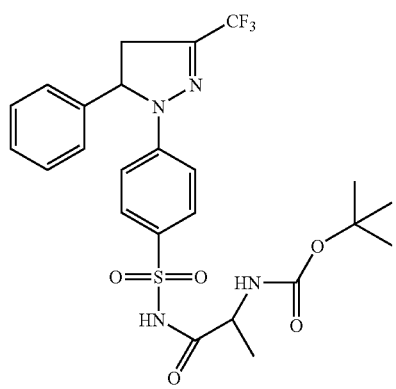

N-t-butoxycarbonyl-L-alanine (1.02 g, 5.4 mmoles) is dissolved in methylene chloride (40 ml) in an inert atmosphere flask and cooled with ice bath. Dicyclohexylcarbodiimide (0.56 g, 2.71 mmoles) is added, all at once, and stirred at 0° C. for 3 hours. Then, a solution of 4-(4,5-dihydro-5-phenyl-3-trifluoromethyl-pyrazole-1-yl) benzenesulphonamide (0.5 g, 1.35 mmoles), 4-dimethylamine-pyridine (82 mg, 0.675 mmoles) and triethylamine (0.25 ml, 1.75 mmoles) in anhydrous tetrahydrofuran (27 ml). is added to the reaction mixture of the corresponding aminoacid anhydride The resulting mixture is stirred overnight at room temperature, cooled and the precipitated dicyclohexylurea is filtered. Ethylic ether is added, it is cooled and the new precipitated dicyclohexylurea is filtered. The ethereal solution is evaporated to dryness and the residue is dissolved in ethyl acetate, which is washed with aqueous solution of 2N hydrochloric acid, saturated solution of sodium chloride, saturated solution of sodium bicarbonate and again with saturated solution of sodium chloride. The organic phase is dried over sodium sulphate, filtered and evaporated to dryness. A crude product is obtained and is crystallised from ethylic-petroleum ether, to give 0.5 g (yield 68%) of product in the form of a beige solid.

(b) N-(2-aminepropionyl)-4-(4,5-dihydro-5-phenyl-3-trifluoromethyl-pyrazole-1-yl)-benzenesulphonamide

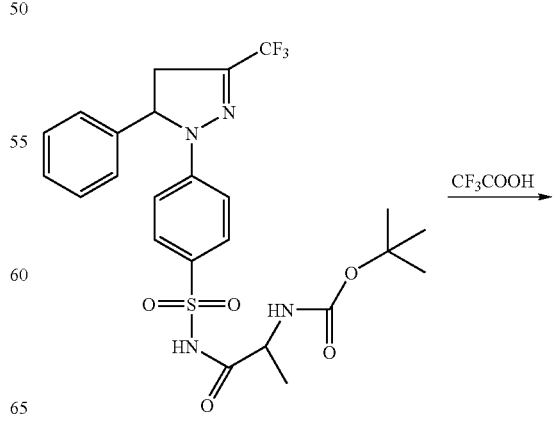

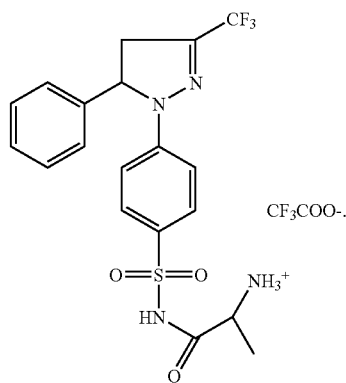

{1-Methyl-2-oxo-2-[4-(5-phenyl-3-trifluoromethyl-4,5-dihydro-pyrazole-1-yl)-benzenesulphonylamine]-ethyl}-carbamic acid t-butilic ester (0.5 g, 0.926 mmoles), dissolved in methylene chloride (25 ml), is cooled to 0° C. with ice bath and trifluoroacetic acid (1.5 ml) is added and stirred until thin layer chromatography control indicates complete disappearance of starting material. The solvent is eliminated in a rotavapor and ethylic ether and water are added to the residue. The remaining solid is filtered and combined with the residue of the ethereal solution, and 0.18 g of product, in the form of a white solid with m.p.=193-198° C., is obtained by crystallization of the mixture from ethylic ether.

$^1$H-NMR (DMSO-$d_6$, δ ppm): 1.2 (d, J=7.0 Hz, 3H), 2.95 (m, 1H), 3.4 (m, 1H), 3.85 (m, 1H), 5.7 (dd, J=6.2 and 12.5 Hz, 1H), 6.95 (d, J=8.8 Hz, 2H), 7.2-7.4 (m, 5H), 7.6 (d, J=8.8 Hz, 2H), 7.7 (s bd, 2H)

Example 6

Preparation of 4-amine-5-oxo-5-[4-(4,5-dihydro-5-phenyl-3-trifluoromethyl-pyrazole-1-yl)-benzene-sulphonylamine] pentanoic acid (Compound 15 of Table 1)

(a) 4-t-butoxycarbonylamine-5-[4-(4,5-dihydro-5-phenyl-3-trifluoromethyl-pyrazole-1-yl)benzenesulphonamine]-5-oxo-pentanoic acid benzylic ester

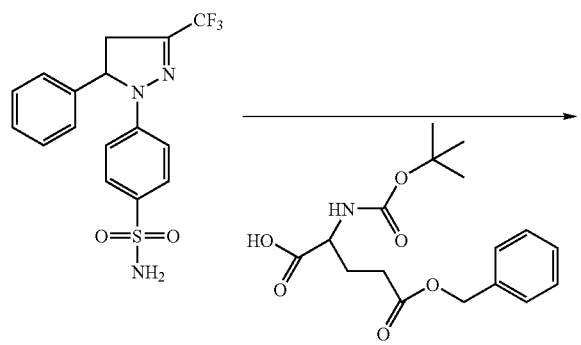

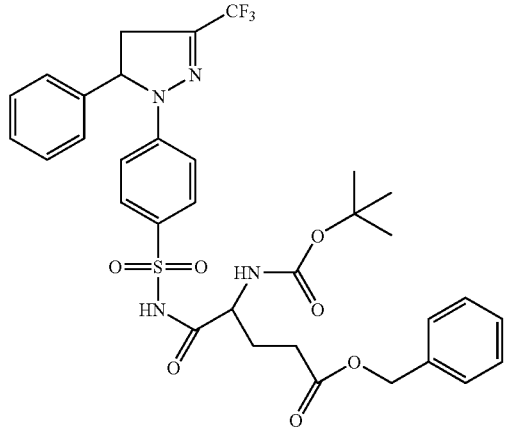

The product is prepared following a process similar to that of step (a) of Example 5, using N-t-butoxycarbonyl-L-glutamic acid 5-benzylic ester.

(b) 4-amine-5-oxo-5-[4-(4.5-dihydro-5-phenyl-3-trifluoromethyl-pyrazole-1-yl)-benzenesulphonylamine] pentanoic acid

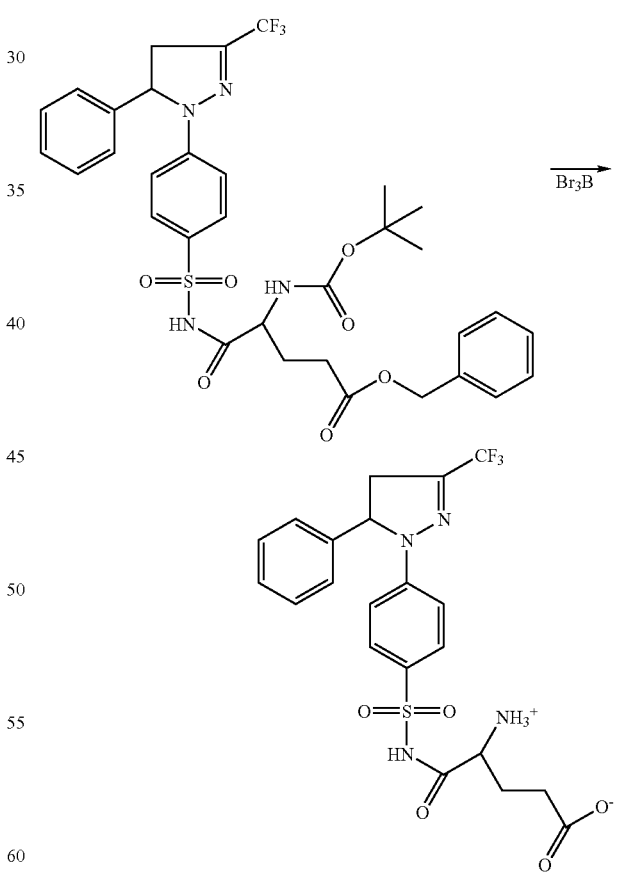

In a flask under dry inert atmosphere, 4-t-butoxy-carbonylamine-5-[4-(4.5-dihydro-5-phenyl-3-trifluoromethyl-pyrazole-1-yl)benzenosulphonamine]-5-oxo-pentanoic acid benzylic ester (0.44 g, 0.64 mmoles) is dissolved in methylene chloride (17 ml) and cooled to −15° C. Then, boron tribromide (3.2 ml, 3.2 mmoles) is added dropwise and stirred, at the same temperature, for 45 minutes. Ice is added to the reaction mixture and the phases are separated. The organic phase is evaporated to dryness, the residue is dissolved in ethyl acetate, washed several times with water, dried over sodium sulphate, filtered and the solvent is evaporated in a rotavapor. The crude product is crystallized from ethanol-water and 0.175 g (yield 47%) of 4-amine-5-oxo-5-[4-(4,5-dihydro-5-phenyl-3-trifluoromethyl-pyrazole-1-yl)-benzenesulphonylamine] pentanoic acid are obtained in the form of a white solid with m.p.=132-135° C.

$^1$H-NMR (DMSO-$d_6$ +TFA, δ ppm): 1.6-2.3 (m, 4H), 2.95 (m, 1H), 3.4 (dd, J=4.9 and 18.3 Hz, 1H), 3.85 (m, 2H), 5.8 (dd, J=6.2 and 12.4 Hz, 1H), 7.05 (d, J=8.8 Hz, 2H), 7.2-7.4 (m, 5H), 7.7 (d, J=8.8 Hz, 2H), 8.2 (s bd, 2H), 12.2 (s bd, 1H)

Table 1 below includes some examples of general formula (I), while Table 2 shows their physical and spectral properties.

Compounds 1, 2, 4, 5, 6, 8, 9, 10, 11, 12, 18, 19, 20, 21, 22, 23, 24, 25, 27, 28, 29, 30, 32, 33, 34, 35, 36, 37, 38 and 39 were prepared in a way similar to that described in Example 1.

Compound 16 was prepared in a way similar to that described in Example 5.

Compound 17 was prepared in a way similar to that described in Example 3.

Compound 26 was prepared from compound 25, in a way similar to that described in Example 2.

TABLE 1

(I)

[Structure: pyrazoline core with CF$_3$ group, two phenyl rings with R and R' substituents]

| Compound | R | R' |
|---|---|---|
| 1 | SO$_2$HN-C(O)-O-CH$_3$ | H |
| 2 | SO$_2$HN-C(O)-CH$_2$-OCOCH$_3$ | H |
| 3 | SO$_2$HN-C(O)-CH$_2$-OH | H |
| 4 | SO$_2$HN-C(O)-O-CH$_2$-CH$_3$ | H |
| 5 | SO$_2$HN-C(O)-O-CH$_2$-CH$_2$-CH$_3$ | H |
| 6 | SO$_2$HN-C(O)-O-CH(CH$_3$)$_2$ | H |
| 7 | SO$_2$HN-C(O)-CH$_2$-CH$_2$-COOH | H |
| 8 | SO$_2$HN-C(O)-O-CH$_2$-CH$_2$-CH$_2$-CH$_3$ | H |

TABLE 1-continued (I) Structure: 1,5-diaryl-3-trifluoromethyl-4,5-dihydropyrazole, with R' on the 5-aryl ring (para) and R on the 1-aryl ring (para).

| Compound | R | R' |
|---|---|---|
| 9 | SO₂HN-C(=O)-O-CH₂-CH(CH₃)CH₃ | H |
| 10 | SO₂HN-C(=O)-CH₂CH₂CH₂-Br | H |
| 11 | SO₂HN-C(=O)-O-CH₂-C(CH₃)₃ | H |
| 12 | SO₂HN-C(=O)-C(CH₃)(CH₂OH)(CH₂OH) | H |
| 13 | SO₂HN-C(=O)-cyclohexyl | H |
| 14 | SO₂HN-C(=O)-CH(NH₂)(CH₃) | H |
| 15 | SO₂HN-C(=O)-CH(NH₂)-CH₂CH₂-COOH | H |
| 16 | SO₂HN-C(=O)-CH(NHBOC)-CH₂CH₂CH₂CH₂-NHBOC | H |
| 17 | SO₂HN-C(=O)-phenyl | H |

TABLE 1-continued (I) Structure: pyrazoline core with CF₃ at 3-position, two phenyl substituents (one with R', one with R on N1).

| Compound | R | R' |
|---|---|---|
| 18 | 4-(phenyl)phenyl-C(O)-NH-SO₂- (biphenyl-4-carbonylsulfonamide) | H |
| 19 | 3-(CH₂Cl)-phenyl-C(O)-NH-SO₂- | H |
| 20 | 4-(OCH₃)-phenyl-C(O)-NH-SO₂- | H |
| 21 | 4-(CN)-phenyl-C(O)-NH-SO₂- | H |
| 22 | 4-(CF₃)-phenyl-C(O)-NH-SO₂- | H |
| 23 | 2-(CF₃)-4-F-phenyl-C(O)-NH-SO₂- | H |
| 24 | 4-(NO₂)-phenyl-C(O)-NH-SO₂- | H |
| 25 | 4-(CO₂CH₃)-phenyl-C(O)-NH-SO₂- | H |
| 26 | 4-(CO₂H)-phenyl-C(O)-NH-SO₂- | H |

TABLE 1-continued (I) Structure: 1,5-diaryl-3-trifluoromethyl-4,5-dihydropyrazole with R' on one phenyl and R on the other.

| Compound | R | R' |
|---|---|---|
| 27 | 2-(trifluoromethyl)phenyl-C(O)-NH-SO2- | H |
| 28 | 4-(methylsulfonyl)phenyl-C(O)-NH-SO2- | H |
| 29 | 4-acetylphenyl-C(O)-NH-SO2- | H |
| 30 | 4-benzoylphenyl-C(O)-NH-SO2- | H |
| 31 | H | -SO2NH-C(O)-O-CH3 |
| 32 | H | -SO2NH-C(O)-CH2CH3 |
| 33 | H | -SO2NH-C(O)-O-CH2CH3 |
| 34 | H | -SO2NH-C(O)-O-CH2CH2CH3 |
| 35 | H | -SO2NH-C(O)-O-CH(CH3)2 |
| 36 | H | -SO2NH-C(O)-C(CH3)3 |

TABLE 1-continued (Structure I: 1,5-diaryl-3-trifluoromethyl-4,5-dihydro-1H-pyrazole, with R' on one phenyl ring and R on the other)

| Compound | R | R' |
|---|---|---|
| 37 | H | SO$_2$HN-C(=O)-O-CH$_2$CH$_2$CH$_2$CH$_3$ |
| 38 | H | SO$_2$HN-C(=O)-O-CH$_2$-C(CH$_3$)$_3$ |
| 39 | H | SO$_2$HN-C(=O)-C$_6$H$_4$-CF$_3$ (para) |

TABLE 2

| Comp. no. | m.p. °C. | $^1$H-NMR-δ ppm |
|---|---|---|
| 1 | 139–144 | (sodium salt, DMSO-d$_6$): 2.9(dd, J=6.2 and 16.3Hz, 1H), 3.2(s, 3H), 3.9(dd, J=12.6 and 16.3Hz, 1H), 5.75(dd, J=6.2 and 12.6Hz, 1H), 6.9(d, J=8.4Hz, 2H), 7.2-7.4(m, 5H), 7.5(d, J=8.4Hz, 2H) |
| 2 | Amorphous | (CDCl$_3$): 1.85(s, 3H), 3.0(dd, J=6.8 and 18.3Hz, 1H), 3.7(dd, J=12.6 and 18.3Hz, 1H), 4.25(s, 2H), 5.4(dd, J=6.8 and 12.6Hz, 1H), 6.9(d, J=8.8Hz, 2H), 7.2-7.4(m, 5H), 7.6(d, J=8.8Hz, 2H) |
| 3 | 138–140 | (CDCl$_3$): 2.6(s bd, 1H), 3.0(dd, J=6.8 and 18.3Hz, 1H), 3.7(dd, J=12.6 and 18.3Hz, 1H), 4.1(s, 2H), 5.5(dd, J=6.8 and 12.6Hz, 1H), 7.05(d, J=9.1Hz, 2H), 7.2-7.4(m, 5H), 7.9(d, J=9.1Hz, 2H), 9.0(s bd, 1H) |
| 4 | Amorphous | (DMSO-d$_6$): 1.0(t, J=7.2Hz, 3H), 2.95(dd, J=5.4 and 18.0Hz, 1H), 3.8(m, 3H), 5.8(dd, J=5.4 and 12.4Hz, 1H), 7.1(d, J=8.9Hz, 2H), 7.2-7.4(m, 5H), 7.7(d, J=8.8Hz, 2H), 11.7(s, 1H) |
| 5 | 220–223 | (sodium salt, DMSO-d$_6$): 0.75(t, J=7Hz, 3H), 1.35(m, 2H), 2.95(dd, J=6.8 and 18.4Hz, 1H), 3.5(t, J=7Hz, 2H), 3.85(dd, J=12.6 and 18.4Hz, 1H), 5.7(dd, J=12.6 and 18.4Hz, 1H), 6.9(d, J=8.8Hz, 2H), 7.2-7.4(m, 5H), 7.5(d, J=8.8Hz, 2H) |
| 6 | 254–258 | (sodium salt, DMSO-d$_6$): 0.95(d, J=6.3Hz, 6H), 2.95(dd, J=6.3 and 18.3Hz, 1H), 3.85(dd, J=12.8 and 18.3Hz, 1H), 4.4(m, 1H), 5.7(dd, J=6.3 and 12.8Hz, 1H), 6.9(d, J=8.8Hz, 2H), 7.2-7.4(m, 5H), 7.5(d, J=8.8Hz, 2H) |
| 7 | Amorphous | (MeOH-d$_4$): 2.5(s, 4H), 3.1(d, J=6.3 and 18.3Hz, 1H), 3.9(dd, J=12.8 and 18.3Hz, 1H), 5.8(dd, J=12.8 and 6.3Hz, 1H), 7.2(d, J=9.0Hz, 2H), 7.3-7.5(m, 5H), 7.8(d, J=9.0Hz, 2H) |
| 8 | 193–196 | (sodium salt, DMSO-d$_6$): 0.8(t, J=7.3Hz, 3H), 1.1-1.4(m, 4H), 2.9(dd, J=6.5 and 18.1Hz, 1H), 3.6(t, J=6.8Hz, 2H), 3.85(dd, J=12.1 and 18.1Hz, 1H), 5.7(dd, J=6.5 and 12.1Hz, 1H), 6.9(d, J=8.7Hz, 2H), 7.2-7.4(m, 5H), 7.5(d, J=8.7Hz, 2H) |
| 9 | 142–145 | (CDCl$_3$): 0.8(d, J=6.8Hz, 6H), 1.8(sept, J=6.8Hz, 1H), 3.0(dd, J=6.6 and 18.3Hz, 1H), 3.7-3.9(dd+d, 3H), 5.45(dd, J=6.6 and 12.6Hz, 1H), 7.1(d, J=9.0Hz, 2H), 7.2-7.4(m, 5H), 7.8(d, J=9.0Hz, 2H) |
| 10 | 164–166 | (CDCl$_3$): 2.0(m, 2H), 2.4(t, J=8.0Hz, 2H), 3.0(dd, J=6.8 and 18.1Hz, 1H), 3.7(dd, J=12.8 and 18.1Hz, 1H), 3.85(t, J=7.1Hz, 2H), 5.4(dd, J=6.8 and 12.8Hz, 1H), 7.05(d, J=8.6Hz, 2H), 7.2-7.4(m, 5H), 7.8(d, J=8.6Hz, 2H) |
| 11 | 240–244 | (sodium salt, DMSO-d$_6$): 0.75(s, 9H), 2.95(dd, J=6.4 and 17.8Hz, 1H), 3.3(s, 2H), 3.8(dd, J=13.0 and 17.8Hz, 1H), 5.7(dd, J=6.4 and 13.0Hz, 1H), 6.9(d, J=8.8Hz, 2H), 7.2-7.4(m, 5H), 7.5(d, J=8.8Hz, 2H) |
| 12 | 187–190 | (sodium salt, DMSO-d$_6$): 0.8(s, 3H), 2.95(m, 1H), 3.2(s, 2H), 3.3(s, 2H), 3.8(m, 1H), 4.8(s bd, 2H), 5.7(m, 1H), 6.9(d, J=8.8Hz, 2H), 7.2-7.4(m, 5H), 7.5(d, J=8.8Hz, 2H) |
| 13 | >280 | (sodium salt, MeOH-d$_4$): 1.25(m, 5H), 1.7(m, 5H), 2.1(m, 1H), 2.9(dd, J=6.9 and 18.3Hz, 1H), 3.8(dd, J=12.5 and 18.3Hz, 1H), 5.6(dd, J=6.9 and 12.5Hz, 1H), 7.0(d, J=8.8Hz, 2H), 7.2-7.4(m, 5H), 7.7(d, J=8.8Hz, 2H) |

TABLE 2-continued

| Comp. no. | m.p. ° C. | $^1$H-NMR-δ ppm |
|---|---|---|
| 14 | 193-198 | (DMSO-d$_6$+TFA): 1.2(d, J=7.0Hz, 3H), 2.95(m, 1H), 3.4(m, 1H), 3.85(m, 1H), 5.7(dd, J=6.2 and 12.5Hz, 1H), 6.95(d, J=8.8Hz, 2H), 7.2-7.4 (m, 5H), 7.6(d, J=8.8Hz, 2H), 7.7(s bd, 2H) |
| 15 | 111-114 | (DMSO-d$_6$+TFA): 1.6-2.3(m, 4H), 2.95(m, 1H), 3.4(dd, J=4.9 and 18.3Hz, 1H), 3.85(m, 1H), 5.8(dd, J=6.2 and 12.4Hz, 1H), 7.05(d, J=8.8Hz, 2H), 7.2-7.4(m, 5H), 7.7(d, J=8.8Hz, 2H), 8.2(s bd, 2H), 12.2(s bd, 1H) |
| 16 | 110-112 | (CDCl$_3$): 1.3-1.6(m, 24H), 2.3-3.0(m, 3H), 3.7 (dd, J=12.6 and 17.2Hz, 1H), 3.9(m, 1H), 4.7(s bd, 1H), 4.9(s bd, 0.5H), 5.3(s bd, 1H), 5.45 (dd, J=6.6 and 12.6Hz, 1H), 5.7(s bd, 0.5H), 7.0 (d, J=8.4Hz, 2H), 7.2-7.4(m, 5H), 7.75(d, J=8.4Hz, 2H) |
| 17 | amorphous | (DMSO-d$_6$): 2.9(dd, J=5.3 and 18.1Hz, 1H), 3.9 (dd, J=12.6 and 18.1Hz, 1H), 5.75(dd, J=5.3 and 12.6Hz, 1H), 7.0(d, J=9.0Hz, 2H), 7.2-7.5(m, 8H), 7.7(d, J=9.0Hz, 2H), 7.8(d, J=8.4Hz, 2H) |
| 18 | >280 | (sodium salt, DMSO-d$_6$): 2.95(m, 1H), 3.9(m, 1H), 5.7(dd, J=6.4 and 12.6Hz, 1H), 6.9(d, J=8.8Hz, 2H), 7.2-7.7(m, 14H), 7.9(d, J=8.8Hz, 2H) |
| 19 | 260-261 | (DMSO-d$_6$): 2.9(dd, J=7.2 and 18.1Hz, 1H), 3.8 (dd, J=13.5 and 18.1Hz, 1H), 4.7(s, 2H), 5.7 (dd, J=7.2 and 13.5Hz, 1H), 6.9(d, J=8.4Hz, 2H), 7.2-7.4(m, 7H), 7.6(d, J=8.4Hz, 2H), 7.8(d, J=7.3Hz, 1H), 7.9(s, 1H) |
| 20 | 180-183 | (CDCl$_3$): 3.0(dd, J=7.0 and 18.3Hz, 1H), 3.7(dd, J=12.7 and 18.3Hz, 1H), 3.8(s, 3H), 5.4(dd, J=7.0 and 12.7Hz, 1H), 6.9(d, J=9.0Hz, 2H), 7.1 (d, J=9.0Hz, 2H), 7.2-7.4(m, 5H), 7.7(d, J=8.9Hz, 2H), 7.9(d, J=9.2Hz, 2H), 8.7(s, 1H) |
| 21 | 195-196 | (CDCl$_3$): 3.0(dd, J=6.8 and 17.6Hz, 1H), 3.7(dd, J=12.6 and 17.6Hz, 1H), 5.4(dd, J=6.8 and 12.6Hz, 1H), 7.1(d, J=9.0Hz, 2H), 7.2-7.4(m, 5H), 7.7(d, J=8.4Hz, 2H), 7.85(d, J=8.4Hz, 2H), 7.9(d, J=9.0Hz, 2H), 9.0(s, 1H) |
| 22 | >280 | (sodium salt, MeOH-d$_4$): 2.9(dd, J=7.0 and 18.1Hz, 1H), 3.6(dd, J=13.0 and 18.1Hz, 1H), 5.3 (dd, J=7.0 and 13.0Hz, 1H), 6.9(d, J=8.8Hz, 2H), 7.1(d, J=6.4Hz, 2H), 7.2-7.3(m, 3H), 7.45(d, J=8.3Hz, 2H), 7.7(d, J=9.0Hz, 2H), 7.9(d, J=8.1Hz, 2H) |
| 23 | >250 | (sodium salt, DMSO-d$_6$): 3.0(dd, J=6.8 and 18.1Hz, 1H), 3.6(m, 1H), 3.0(dd, J=12.3 and 18.1Hz, 1H), 5.75(dd, J=6.8 and 12.3Hz, 1H), 6.9(d, J=8.8Hz, 2H), 7.2-7.5(m, 8H), 7.6(d, J=8.8Hz, 2H) |
| 24 | 275(desc) | (sodium salt, DMSO-d$_6$): 2.9(dd, J=6.2 and 19.0Hz, 1H), 3.9(dd, J=12.5 and 19.0Hz, 1H), 5.7(dd, J=6.2 and 12.5Hz, 1H), 6.9(d, J=8.8Hz, 2H), 7.2-7.35(m, 5H), 7.65(d, J=8.8Hz, 2H), 8.05(d, J=8.2Hz, 2H), 8.15(d, J=8.2Hz, 2H) |
| 25 | >280 | (sodium salt, DMSO-d$_6$): 2.9(m, 1H), 3.85-4.0 (m+s, 4H), 5.7(dd, J=7.0 and 16.8Hz, 1H), 6.9 (d, J=8.8Hz, 2H), 7.2-7.4(m, 5H), 7.6(d, J=8.8Hz, 2H), 7.85(d, J=7.9Hz, 2H), 7.9(d, J=7.9Hz, 2H) |
| 26 | Amorphous | (DMSO-d$_6$): 3.0(dd, J=6.4 and 18.1Hz, 1H), 3.7 (dd, J=12.7 and 18.1Hz, 1H), 5.4(dd, J=6.4 and 12.7Hz, 1H), 7.1(d, J=9.0Hz, 2H), 7.2-7.4(m, 5H), 7.9(d, J=9.0Hz, 2H), 8.0(d, J=8.4Hz, 2H), 8.2(d, J=8.5Hz, 2H), 10.2(s, 1H) |
| 27 | 125-127 | (sodium salt, DMSO-d$_6$): 3.0(dd, J=5.7 and 17.6Hz, 1H), 3.9(dd, J=12.6 and 17.6Hz, 1H), 5.8(dd, J=5.7 and 12.6Hz, 1H), 7.0(d, J=8.9Hz, 2H), 7.2-7.6(m, 9H), 7.65(d, J=8.8Hz, 2H) |
| 28 | >280 | (sodium salt, DMSO-d$_6$): 2.9(dd, J=6.9 and 18.4Hz, 1H), 3.2(s, 3H), 3.85(dd, J=12.8 and 18.4Hz, 1H), 5.7(dd, J=6.9 and 12.8Hz, 1H), 6.9(d, J=8.8Hz, 2H), 7.2-7.4(m, 5H), 7.6(d, J=8.8Hz, 2H), 7.8(d, J=8.6Hz, 2H), 8.0(d, J=8.6Hz, 2H) |
| 29 | >280 | (sodium salt, DMSO-d$_6$): 2.5(s, 3H), 2.9(m, 1H), 3.85(m, 1H), 5.7(dd, J=6.8 and 12.2Hz, 1H), 6.9(d, J=8.9Hz, 2H), 7.2-7.4(m, 5H), 7.6 (d, J=8.9Hz, 2H), 7.85(d, J=8.4Hz, 2H), 7.9 (d, J=8.4Hz, 2H) |
| 30 | >280 | (sodium salt, DMSO-d$_6$): 2.95(dd, J=6.7 and 16.8Hz, 1H), 3.85(dd, J=12.0 and 16.8Hz, 1H), 5.7(dd, J=6.7 and 12.0Hz, 1H), 6.9(d, J=8.8Hz, 2H), 7.2-7.4(m, 5H), 7.5-7.7(m, 9H), 8.0(d, J=8.2Hz, 2H) |
| 31 | 244-247 | (sodium salt, DMSO-d$_6$): 2.9(dd, J=6.5 and 18.2Hz, 1H), 3.2(s, 3H), 3.8(dd, J=18.2 and 12.8Hz, 1H), 5.7(dd, J=6.5 and 12.8Hz, 1H), 6.8(t, J=7.3Hz, 1H), 6.95(d, J=7.7Hz, 2H), 7.15-7.25(m, 4H), 7.7(d, J=8.2Hz, 2H) |
| 32 | >280 | (sodium salt, DMSO-d$_6$): 0.8(t, J=7.4Hz, 3H), 1.85(q, J=7.6Hz, 2H), 2.9(dd, J=6.9 and 18.6Hz, 1H), 3.8(dd, J=12.9 and 18.6Hz, 1H), 5.7(dd, J=6.9 and 12.9Hz, 1H), 6.8(t, J=7.5 Hz, 1H), 6.95(d, J=6.5Hz, 2H), 7.15-7.25(m, 4H), 7.7(d, J=7.5Hz, 2H) |
| 33 | 270-277 | (sodium salt, DMSO-d$_6$): 1.0(t, J=7.2Hz, 3H), 2.95(dd, J=7.5 and 17.8Hz, 1H), 3.6(q, J=7.2Hz, 2H), 3.8(m, 1H), 5.7(dd, J=7.5 and 13.2Hz, 1H), 6.8(m, 1H), 6.9(d, J=8.2Hz, 2H), 7.15-7.25(m, 4H), 7.7(d, J=8.2Hz, 2H) |
| 34 | 239-245 | (sodium salt, DMSO-d$_6$): 0.65(t, J=7.5Hz, 3H), 1.4(m, 2H), 2.9(dd, J=7.0 and 18.2Hz, 1H), 3.8(dd+t, J=6.6. 12.9 and 18.2Hz, 3H), 5.7 (dd, J=7.0 and 12.9Hz, 1H), 6.8(t, J=7.3Hz, 1H), 6.9(d, J=7.8Hz, 2H), 7.1(t, J=8.8Hz, 2H), 7.45(d, J=8.4Hz, 2H), 7.8(d, J=8.4Hz, 2H) |
| 35 | 254-599 | (sodium salt, MeOH-d$_4$): 1.2(d, J=6.0Hz, 6H), 3.0(dd, J=6.3 and 17.6Hz, 1H), 3.8(dd, J= 12.5 and 17.6Hz, 1H), 4.7(m, 1H), 5.7(dd, J=6.3 and 12.5Hz, 1H), 6.9(t, J=7.2Hz, 1H), 7.0(d, J=7.9Hz, 2H), 7.2(t, J=8.3Hz, 2H), 7.45(d, J=8.3Hz, 2H), 7.9(d, J=8.3Hz, 2H) |
| 36 | >280 | (sodium salt, DMSO-d$_6$): 2.9(dd, J=7.3 and 17.9Hz, 1H), 3.8(dd, J=12.7 and 17.9Hz, 1H), 5.7(dd, J=7.3 and 12.7Hz, 1H), 6.8(t, J=7.3Hz, 1H), 6.9(d, J=8.6Hz, 2H), 7.15-7.25 (m, 4H), 7.65(d, J=8.2Hz, 2H) |
| 37 | 223-230 | (sodium salt, MeOH-d$_4$): 0.95(t, J=7.3Hz, 3H), 1.4(m, 2H), 1.6(m, 2H), 3.0(dd, J=7.3 and 17.9Hz, 1H), 3.9(dd+t, J=6.4. 12.7 and 17.9Hz, 3H), 5.7(dd, J=7.3 and 12.7Hz, 1H), 6.9(t, J=7.3Hz, 1H), 7.05(d, J=7.9Hz, 2H), 7.2(t, J=8.5Hz, 2H), 7.45(d, J=8.3Hz, 2H), 7.95(d, J=8.3Hz, 2H) |
| 38 | 254-259 | (sodium salt, DMSO-d$_6$): 0.75(s, 9H), 2.95(m, 1H), 3.3(s, 3H), 3.8(m, 1H), 5.7(dd, J=6.2 and 12.1Hz, 1H), 6.8(t, J=7.6Hz, 1H), 6.9(d, J=7.6Hz, 2H), 7.15-7.25(m, 4H), 7.65(d, J=7.6Hz, 2H) |
| 39 | 280 (desc) | (sodium salt, DMSO-d$_6$): 2.9(dd, J=6.3 and 18.1Hz,. 1H), 3.9(dd, J=13.5 and 18.1Hz, 1H), 5.7(dd, J=6.3 and 13.5Hz, 1H), 6.8(m, 1H), 6.9 (d, J=8.3Hz, 2H), 7.2(m, 2H), 7.25(d, J=8.2Hz, 2H), 7.6(d, J=8.2Hz, 2H), 7.8(d, J=8.1Hz, 2H), 8.0(d, J=8.3Hz, 2H) |

Biological Activity

Analgesia Test on Rats

The analgesic activity of the compounds of the invention is tested as described in the publication by K. Hargreaves et al., Pain, 32. 77-88. (1988).

Briefly, the rats are transferred to the experimentation laboratory, where they remain in groups of five in Makrolon cages with barred floors to prevent coprophagy. At the start of the experiment, water and food were removed and animals weighed and labelled appropriately.

Each rat receives by subplantar injection 0.1 ml of sterile saline solution in the rear left leg, followed by 0.1 ml 2% (weight/volume) carrageenan suspension in sterile saline solution in the rear right leg.

Three hours following the subplantar injections of carrageenan and vehicle, each rat was intravenously administered with compounds to be tested, dissolved in sterile saline serum, at a dose of 1 ml per kg of body weight. Then after administration of compounds, analgesic activity values were read. For this purpose, rats were transferred to the methacrylate chambers of an analgesimeter with a glass floor. Once the period of acclimatisation in the chambers had elapsed (i.e., after 5 minutes), an infrared radiation lamp capable of producing thermal stimulation was placed under the rats' legs. Readings of analgesic activity were taken at 15, 30, 60 and 120 minutes following administration of the products or their vehicle.

The thermal stimulus, calibrated beforehand to 10 amperes, is applied to each of the rear legs at intervals of at least 1 minute. The response of the rats to the pain consists in raising the leg, thus avoiding contact with the floor. Simultaneously, the infrared light goes out automatically and the device's digital screen shows the latency time in seconds.

Table 3 shows the analgesic activity values of some of the compounds of this invention, in accordance with the test described above.

TABLE 3

| Compound | % activity 2.5 mg/kg i.v. | |
| --- | --- | --- |
|  | At 30 min. | At 120 min. |
| 3 | 41 | 40 |
| 4 | 78 | 48 |
| 22 | 72 | 76 |
| 25 | 67 | 66 |
| 31 | 76 | 49 |
| 32 | 72 | 51 |
| 37 | 68 | 75 |
| 39 | 92 | 57 |

The invention claimed is:

1. Pyrazoline derivative of general formula (I)

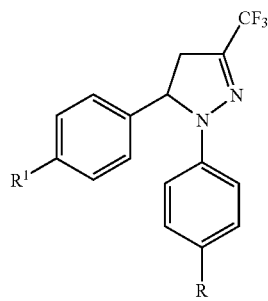

(I)

in which R and $R^1$ are different from each other and are selected from a hydrogen or a

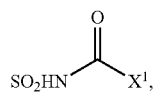

provided that when $R^1$ is hydrogen and R is a

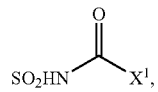

$X^1$ is an alkyl substituted by at least one group selected from a halogen, a hydroxy, an amine, a carboxy, a carboxyalkyl, an acylamine, or a $CONH_2$; a cycloalkyl, optionally at least monosubstituted; a heterocycle; a $-OX^2$; a

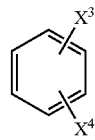

or a heteroaryl, optionally at least monosubstituted;

$X^2$ is an alkyl optionally substituted with one or more substituents selected independently from a halogen, a hydroxy, an alkoxyl, a cycloalkyl, optionally at least monosubstituted; a heterocycle; an aryl or a heteroaryl, optionally at least monosubstituted;

$X^3$ and $X^4$ are the same as or different from each other and are selected from a hydrogen; a halogen; an amine; a nitro; a cyano; an alkyl optionally substituted with one or more substituents selected independently from a halogen, a hydroxy or an alkoxyl; a $-CO_2X^5$; a $-COX^6$; a $-SO_2X^7$; an aryl or an heteroaryl, optionally at least monosubstituted;

$X^5$ is a hydrogen or an alkyl, optionally substituted with one or more substitutents selected independently from a halogen, a hydroxy or an alkoxyl;

$X^6$ is an alkyl optionally substituted with one or more substituents selected independently from a halogen, a hydroxy or an alkoxyl; a cycloalkyl optionally at least monosubstituted; a heterocycle; an aryl or heteroaryl, optionally at least monosubstituted; and $X^7$ is an alkyl; a cycloalkyl; an aryl; or a heteroaryl, optionally at least monosubstituted; and provided that when R is hydrogen and $R^1$ is a

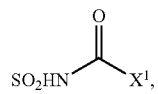

$X^1$ is an alkyl comprising at least two carbon atoms, optionally substituted with at least one group selected from a halogen, a hydroxy, an amine, a carboxy, a carboxyalkyl, an acylamine or a $CONH_2$; a cycloalkyl, optionally at least monosubstituted; a heterocycle; a $-OX^2$; a

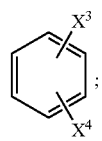

or a heteroaryl, optionally at least monosubstituted;

$X^2$, $X^3$, $X^4$, $X^5$, $X^6$ and $X^7$ are defined above;

and a pharmaceutically acceptable salt thereof, a stereoisomer thereof; a racemate thereof, or a mixture thereof in any mixture ratio.

2. The pyrazoline derivative of according to claim 1, in which when $R^1$ is hydrogen and R is a

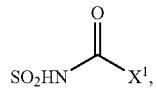

$X^1$ is an alkyl substituted by at least one group selected from a halogen, a hydroxy, an amine, a carboxy, a carboxyalkyl; or an acylamine; a cycloalkyl; a —$OX^2$ or a

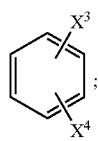

$X^2$ is an alkyl;
$X^3$ and $X^4$ are the same as or different from each other and are selected from a hydrogen; an aryl group optionally at least monosubstituted; a haloalkyl; an alkoxyl; a halogen; a nitro; a cyano; a —$CO_2X^5$; a —$COX^6$; or a —$SO_2X^7$;
$X^5$ is a hydrogen or an alkyl;
$X^6$ is an alkyl or an aryl optionally at least monosubstituted; and
$X^7$ is an alkyl;
and provided that when R is hydrogen and $R^1$ is a

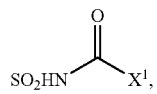

$X^1$ is an alkyl comprising at least two carbon atoms; a —$OX^2$; or an aryl optionally at least monosubstituted; and $X^2$ is an alkyl;
and a pharmaceutically acceptable salt thereof, a stereoisomer thereof, a racemate thereof, or a mixture thereof in any mixture ratio.

3. The pyrazoline derivative according to claim 1, in which when $R^1$ is a hydrogen; and R is a

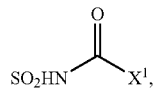

$X^1$ is an alkyl substituted by at least one group from a halogen, a hydroxy, an amine, a carboxy, a carboxyalkyl or an acylamine.

4. The pyrazoline derivative according to claim 1, in which when $R^1$ is a hydrogen; and R is a

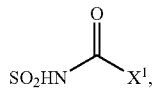

$X^1$ is a cycloalkyl.

5. The pyrazoline derivative according to claim 1, in which when $R^1$ is a hydrogen; and R is a

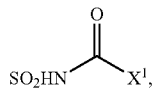

$X^1$ is a —$OX^2$ and $X^2$ is an alkyl.

6. The pyrazoline derivative according to claim 1, in which when $R^1$ is hydrogen; and R is a

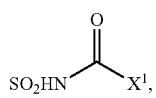

$X^1$ is a

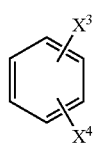

and
$X^3$ and $X^4$ are the same as or different from each other and are selected from a hydrogen; an aryl optionally at least monosubstituted; a haloalkyl; an alkoxyl; a halogen; a nitro; a cyano; a —$CO_2X^5$; a —$COX^6$; or a —$SO_2X^7$;
$X^5$ is a hydrogen or an alkyl;
$X^6$ is an alkyl or an aryl optionally at least monosubstituted; and
$X^7$ is an alkyl.

7. The pyrazoline derivative according to claim 1, in which when R is a hydrogen; and $R^1$ is a

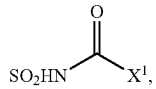

$X^1$ is an alkyl comprising at least two carbon atoms.

8. The pyrazoline derivative according to claim 1, in which when R is a hydrogen and $R^1$ is a

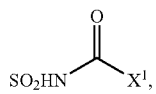

$X^1$ is a —$OX^2$ and $X^2$ is an alkyl.

9. The pyrazoline derivative according to claim 1, in which when R is a hydrogen and R¹ is a

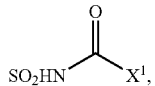

X¹ is an aryl optionally at least monosubstituted.

10. The pyrazoline derivative according to claim 1, in which X¹ is selected from:
—CH₂OH,
—(CH₂)₄—Br,

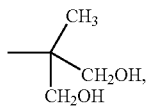

—CH(NH₂)—CH₃,
—CH(NH₂)—(CH₂)₂—COOH,
—CH(NHBOC)—(CH₂)₄(NHBOC),
—CH₂CH₂COOH, or
—CH₂OCOCH₃.

11. The pyrazoline derivative according to claim 1, in which X¹ is a cyclohexyl.

12. The pyrazoline derivative according to claim 1, in which X² is selected from a methyl, an ethyl, a propyl, an isopropyl, a butyl, an isobutyl or a neopentyl.

13. The pyrazoline derivative according to claim 1, in which X³ and X⁴ are selected from a hydrogen, a fluoro, a nitro, a CN, a chloromethyl, a trifluoromethyl, a methoxyl, or a phenyl;
X⁵ is a hydrogen or a methyl;
X⁶ is a methyl or a phenyl; and
X⁷ is a methyl.

14. The pyrazoline derivative according to claim 1, in which when X¹ is an ethyl or a tert-butyl.

15. The pyrazoline derivative according to claim 1, in which X² is a methyl, an ethyl, a propyl, an isopropyl, a butyl or a neopentyl.

16. The pyrazoline derivative according to claim 1, in which X¹ is a trifluoromethylphenyl.

17. The pyrazoline derivative according to claim 1, wherein the pyrazoline derivative is:
  *N-Methoxycarbonyl-4-(4,5-dihydro-5-phenyl-3-trifluoromethyl-pyrazole-1-yl)-benzenesulphonamide;
  *N-((2-Acethyloxi)acetyl)-4-(4,5-dihydro-5-phenyl-3-trifluoromethyl-pyrazole-1-yl)-benzenesulphonamide;
  *N-(2-Hydroxyacetyl)-4-(4,5-dihydro-5-phenyl-3-trifluoromethyl-pyrazole-1-yl)-benzenesulphonamide;
  *N-Ethyloxicarbonyl-4-(4,5-dihydro-5-phenyl-3-trifluoromethyl-pyrazole-1-yl)-benzenesulphonamide;
  *N-Propyloxicarbonyl-4-(4,5-dihydro-5-phenyl-3-trifluoromethyl-pyrazole-1-yl)-benzenesulphonamide;
  *N-Isopropyloxicarbonyl-4-(4,5-dihydro-5-phenyl-3-trifluoromethyl-pyrazole-1-yl)-benzenesulphonamide;
  *4-oxo-4-[4-(4,5-dihydro-5-phenyl-3-trifluoromethyl-pyrazole-1-yl)-benzenesulphonylamine] butyric acid;
  *N-Butyloxicarbonyl-4-(4,5-dihydro-5-phenyl-3-trifluoromethyl-pyrazole-1-yl)-benzenesulphonamide;
  *N-(2-Methylpropionyloxicarbonyl)-4-(4,5-dihydro-5-phenyl-3-trifluoromethyl-pyrazole-1-yl)-benzenesulphonamide;
  *N-(5-Bromopentanoyl)-4-(4,5-dihydro-5-phenyl-3-trifluoromethyl-pyrazole-1-yl)-benzenesulphonamide;
  *N-(2,2-Dimethylpropyloxicarbonyl)-4-(4,5-dihydro-5-phenyl-3-trifluoromethyl-pyrazole-1-yl)-benzenesulphonamide;
  *N-(2-Hydroxymethyl-2-methyl-3-hydroxypropionyl)-4-(4,5-dihydro-5-phenyl-3-trifluoromethyl-pyrazole-1-yl)-benzenesulphonamide;
  *N-(Cyclohexanocarbonyl)-4-(4,5-dihydro-5-phenyl-3-trifluoromethyl-pyrazole-1-yl)-benzenesulphonamide;
  *N-(2-Aminepropionyl)-4-(4,5-dihydro-5-phenyl-3-trifluoromethyl-pyrazole-1-yl)-benzenesulphonamide;
  *4-Amine-5-oxo-5-[4-(4,5-dihydro-5-phenyl-3-tri-fluoromethyl-pyrazole-1-yl)-benzenesulphonylamine] pentanoic acid;
  *N-[(2,6-diterbutoxycarbonylamine)hexanoyl]-4-(4,5-dihydro-5-phenyl-3-trifluoromethyl-pyrazole-1-yl)-benzenesulphonamide;
  *N-Benzoyl-4-(4,5-dihydro-5-phenyl-3-trifluoromethyl-pyrazole-1-yl)-benzenesulphonamide;
  *N-(Biphenyl-4-carbonyl)-4-(4,5-dihydro-5-phenyl-3-trifluoromethyl-pyrazole-1-yl)-benzenesulphonamide;
  *N-(3-Chloromethylbenzoyl)-4-(4,5-dihydro-5-phenyl-3-trifluoromethyl-pyrazole-1-yl)-benzenesulphonamide;
  *N-(4-Methoxybenzoyl)-4-(4,5-dihydro-5-phenyl-3-trifluoromethyl-pyrazole-1-yl)-benzenesulphonamide;
  *N-(4-Cyanobenzoyl)-4-(4,5-dihydro-5-phenyl-3-trifluoromethyl-pyrazole-1-yl)-benzenesulphonamide;
  *N-(4-Trifluoromethylbenzoyl)-4-(4,5-dihydro-5-phenyl-3-trifluoromethyl-pyrazole-1-yl)-benzenesulphonamide;
  *N-(4-Fluoro-2-trifluoromethylbenzoyl)-4-(4,5-dihydro-5-phenyl-3-trifluoromethyl-pyrazole-1-yl)-benzenesulphonamide;
  *N-(4-Nitrobenzoyl)-4-(4,5-dihydro-5-phenyl-3-trifluoromethyl-pyrazole-1-yl)-benzenesulphonamide;
  *4-[4-(4,5-dihydro-5-phenyl-3-trifluoromethyl-pyrazole-1-yl)-benzenesulphonylamine] benzoic acid methylic ester;
  *4-[4-(4,5-dihydro-5-phenyl-3-trifluoromethyl-pyrazole-1-yl)-benzenesulphonylaminecarbonyl] benzoic acid;
  *N-(2-Trifluoromethylbenzoyl)-4-(4,5-dihydro-5-phenyl-3-trifluoromethyl-pyrazole-1-yl)-benzenesulphonamide;
  *N-(4-Metansulphonylbenzoyl)-4-(4,5-dihydro-5-phenyl-3-trifluoromethyl-pyrazole-1-yl)-benzenesulphonamide;
  *N-(4-Acetyl-benzoyl)-4-(4,5-dihydro-5-phenyl-3-trifluoromethyl-pyrazole-1-yl)-benzenesulphonamide;
  *N-(4-Benzoyl-benzoyl)-4-(4,5-dihydro-5-phenyl-3-trifluoromethyl-pyrazole-1-yl)-benzenesulphonamide;
  *N-Methoxycarbonyl-4-(4,5-dihydro-1-phenyl-3-trifluoromethyl-1H-pyrazole-5-yl)benzenesulphonamide;
  *N-Propionyl-4-(4,5-dihydro-1-phenyl-3-trifluoromethyl-1H-pyrazole-5-yl)benzenesulphonamide;
  *N-Ethoxycarbonyl-4-(4,5-dihydro-1-phenyl-3-trifluoromethyl-1H-pyrazole-5-yl)benzenesulphonamide;
  *N-Propoxycarbonyl-4-(4,5-dihydro-1-phenyl-3-trifluoromethyl-1H-pyrazole-5-yl)benzenesulphonamide;
  *N-Isopropoxycarbonyl-4-(4,5-dihydro-1-phenyl-3-trifluoromethyl-1H-pyrazole-5-yl)benzenesulphonamide;
  *N-(2,2-Dimethyl)propionyl-4-(4,5-dihydro-1-phenyl-3-trifluoromethyl-1H-pyrazole-5-yl)benzenesulphonamide;
  *N-Butoxycarbonyl-4-(4,5-dihydro-1-phenyl-3-trifluoromethyl-1H-pyrazole-5-yl)benzenesulphonamide;
  *N-(2,2-Dimethyl)propoxycarbonyl-4-(4,5-dihydro-1-phenyl-3-trifluoromethyl-1H-pyrazole-5-yl)benzenesulphonamide; and

*N-(4-Trifluoromethyl)benzoil-4-(4,5-dihydro-1-phenyl-3-trifluoromethyl-1H-pyrazole-5-yl)benzenesulphonamide;
or a pharmaceutically acceptable salt thereof.

18. The pyrazoline derivative according to claim 1, wherein the pharmaceutical acceptable salt is a sodium salt.

19. A process for the preparation of the pyrazoline derivative according to claim 1, in which R is hydrogen and $R^1$ is a

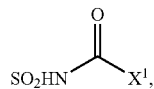

comprising the reaction of a compound of formula (VII);

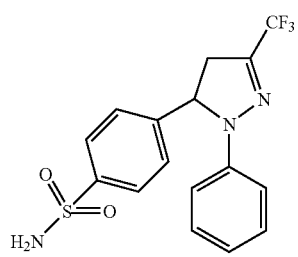
(VII)

with a compound of formula (VIII):

$X^1CO-A$     (VIII)

wherein A is a halogen or a —O—$COX^1$; and $X^1$ is an alkyl comprising at least two carbon atoms, optionally substituted with at least one group selected from a halogen, a hydroxy, an amine, a carboxy, a carboxyalkyl, an acylamine, or a —$CONH_2$; a cycloalkyl, optionally at least monosubstituted; a heterocycle; an —$OX^2$; a

or a heteroaryl, optionally at least monosubstituted;

with $X^2$; $X^3$ and $X^4$ are defined in claim 1 or 2.

20. The process according to claim 19, in which the compound of formula (VIII) is an acyl chloride or an acyl bromide.

21. The process according to claim 19, in which the compound of formula (VIII) is a chloroformiate.

22. The process according to claim 19, in which the compound of formula (VIII) is an acyl anhydride.

23. A process for the preparation of the pyrazoline derivative according to claim 1, in which $R^1$ is a hydrogen and R is a

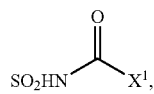

comprising the reaction of a compound of formula (III):

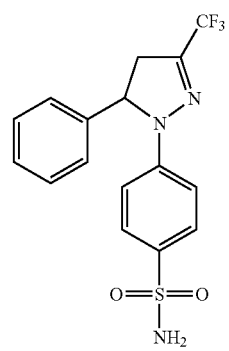
(III)

with a compound of formula (VIII):

$X^1CO-A$     (VIII)

wherein A is a halogen or a —O—$COX^1$; and $X^1$ is an alkyl substituted by at least one group selected from a halogen, a hydroxy, an amine, a carboxy, a carboxyalkyl, a acylamine or a $CONH_2$; a cycloalkyl, optionally at least monosubstituted; a heterocycle; an —$OX^2$; a

or a heteroaryl, optionally at least monosubstituted;

$X^2$, $X^3$ and $X^4$ are defined in claim 1 or 2.

24. The process according to claim 23, in which the compound of formula (VIII) is a an acyl chloride or an acyl bromide.

25. The process according to claim 23, in which the compound of formula (VIII) is a chloroformiate.

26. The process according to claim 23, in which the compound of formula (VIII) is an acyl of an anhydride.

27. A pharmaceutical composition comprising at least one pyrazoline derivative according to claim 1.

28. The pharmaceutical composition according to claim 27, further comprising least one pharmaceutically acceptable diluent or adjuvant.

29. The pharmaceutical composition according to claim 27, wherein the at least one pyrazoline derivative is a salt.

30. The pharmaceutical composition according to claim 29, wherein the salt is a sodium salt.

31. A method for the treatment of inflammation in a animal comprising administering to the animal the pyrazoline derivative according to claim 1.

32. A method for the treatment of pain in a animal comprising administering to the animal the pyrazoline derivative according to claim 1.

33. The method according to claim 31, wherein the pyrazoline derivative is a salt.

34. The method according to claim 33, wherein the salt is a sodium salt.

35. The method according to claim 31, in which the administering is by injection.

36. The method according to claim 31, in which the administering is by infusion.

37. The method according to claim 35, in which the administering is endovenously.

38. The method according to claim 35, in which the administering is intraperitoneally.

39. The method according to claim 35, in which the administering is subcutaneously.

40. The method according to claim 35, in which the administering is intramuscularly.

41. The method according to claim 31, in which the administering is by applying a collyrium.

42. The method of a pyrazoline derivative according to claim 31, in which the animal is a mammal.

43. The method of a pyrazoline derivative according to claim 42, in which the mammal is a human.

44. The pyrazoline derivative according to claim 1, wherein the stereoisomer is an enantiomer or a diastereomer.

45. The pyrazoline derivative according to claim 2, wherein the stereoisomer is an enantiomer or a diastereomer.

* * * * *